US012648977B2

(12) United States Patent
McCown et al.

(10) Patent No.: US 12,648,977 B2
(45) Date of Patent: *Jun. 9, 2026

(54) GENERATION OF NEURONS BY REPROGRAMMING OF OLIGODENDROCYTES AND OLIGODENDROCYTE PRECURSOR CELLS

(71) Applicant: The University of North Carolina at Chapel Hill, Chapel Hill, NC (US)

(72) Inventors: Thomas McCown, Carrboro, NC (US); Marc Weinberg, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/740,874

(22) Filed: Jun. 12, 2024

(65) Prior Publication Data
US 2025/0382635 A1      Dec. 18, 2025

Related U.S. Application Data

(63) Continuation of application No. 17/542,150, filed on Dec. 3, 2021, which is a continuation of application No. 16/330,663, filed as application No. PCT/US2017/050242 on Sep. 6, 2017, now abandoned.

(60) Provisional application No. 62/383,802, filed on Sep. 6, 2016.

(51) Int. Cl.
| | |
|---|---|
| *C12N 15/86* | (2006.01) |
| *A61K 9/00* | (2006.01) |
| *A61K 31/7105* | (2006.01) |
| *A61K 31/713* | (2006.01) |
| *A61K 35/76* | (2015.01) |
| *A61K 45/06* | (2006.01) |
| *A61P 25/00* | (2006.01) |
| *A61P 25/14* | (2006.01) |
| *A61P 25/16* | (2006.01) |
| *A61P 25/28* | (2006.01) |
| *C12N 5/079* | (2010.01) |
| *C12N 5/0793* | (2010.01) |
| *C12N 15/113* | (2010.01) |

(52) U.S. Cl.
CPC ............ *A61K 35/76* (2013.01); *A61K 9/0019* (2013.01); *A61K 31/7105* (2013.01); *A61K 31/713* (2013.01); *A61K 45/06* (2013.01); *A61P 25/00* (2018.01); *A61P 25/14* (2018.01); *A61P 25/16* (2018.01); *A61P 25/28* (2018.01); *C12N 5/0619* (2013.01); *C12N 5/0622* (2013.01); *C12N 15/113* (2013.01); *C12N 15/86* (2013.01); *C12N 2310/11* (2013.01); *C12N 2310/111* (2013.01); *C12N 2310/122* (2013.01); *C12N 2310/14* (2013.01); *C12N 2310/141* (2013.01); *C12N 2330/51* (2013.01);

*C12N 2750/14141* (2013.01); *C12N 2750/14143* (2013.01); *C12N 2750/14145* (2013.01); *C12N 2750/14171* (2013.01); *C12N 2830/008* (2013.01)

(58) Field of Classification Search
CPC ...................................................... C12N 15/86
See application file for complete search history.

(56) References Cited

U.S. PATENT DOCUMENTS

| | | | | |
|---|---|---|---|---|
| 8,137,910 | B2 * | 3/2012 | Cullen | C12N 15/8241 |
| | | | | 435/375 |
| 8,461,315 | B2 * | 6/2013 | Benwich | C12Q 1/6876 |
| | | | | 536/23.1 |
| 9,481,864 | B1 * | 11/2016 | Kamath | A61P 25/28 |
| 9,636,370 | B2 * | 5/2017 | McCown | C07K 14/005 |
| 10,561,743 | B2 * | 2/2020 | Gray | A61P 7/00 |
| 11,491,242 | B2 * | 11/2022 | Gray | C12N 15/62 |
| 2007/0031844 | A1 * | 2/2007 | Khvorova | A61P 3/10 |
| | | | | 435/6.13 |
| 2009/0325200 | A1 | 12/2009 | Beck et al. | |
| 2015/0238550 | A1 * | 8/2015 | McCown | A61P 35/00 |
| | | | | 435/235.1 |
| 2015/0299698 | A1 | 10/2015 | Fu et al. | |
| 2016/0160184 | A1 | 6/2016 | Ahlfors et al. | |
| 2017/0183662 | A1 | 6/2017 | Carroll et al. | |

FOREIGN PATENT DOCUMENTS

WO      2011109823 A1      9/2011

OTHER PUBLICATIONS

*Homo sapiens* polypyrimidine tract binding protein 1 (PTBP1), transcript variant 4, mRNA https://www.ncbi.nlm.nih.gov/nuccore/NM_001411140.1?report=fasta (Year: 2024).*
Angbart et al. Design of siRNA Therapeutics from the Molecular Scale. Pharmaceuticals 6: 440-468. (Year: 2013).*
Xue et al. Direct Conversion of Fibroblasts to Neurons by Reprogramming PTB-Regulated MicroRNA Circuits. Cell 152: 82-96. (Year: 2013).*
He et al. Knockdown of polypyrimidine tract-binding protein suppresses ovarian tumor cell growth and invasiveness in vitro. Oncogene 26: 4961-4968. (Year: 2007).*

(Continued)

*Primary Examiner* — James D Schultz
*Assistant Examiner* — Keenan A Bates
(74) *Attorney, Agent, or Firm* — Myers Bigel, P.A.

(57)                    ABSTRACT

The invention relates to products and methods for transdifferentiating oligodendrocytes and/or oligodendrocyte precursor cells to neurons. The invention further relates to methods of treating central nervous system disorders and conditions.

11 Claims, 5 Drawing Sheets

Specification includes a Sequence Listing.

(56)                References Cited

OTHER PUBLICATIONS

Silber et al. miR-124 and miR-137 inhibit proliferation of glioblastoma multiforme cells and induce differentiation of brain tumor stem cells. BMC Medicine 6: 1-17. (Year: 2008).*

Supplemental He et al. Knockdown of polypyrimidine tract-binding protein suppresses ovarian tumor cell growth and invasiveness in vitro. Oncogene 26: 4961-4968. (Year: 2007).*

GenBank: BC004383.1, *Homo sapiens* polypyrimidine tract binding protein 1, mRNA (cDNA clone MGC:10830 Image:361 5251), complete cds, accessed and retrieved from www.ncbi.nlm.nih.gov on May 4, 2021. (Year: 2006).

NBCI Reference Sequence: NM_021205.6, *Homo sapiens* ras homolog family member U (RHOU), transcript variant 1, mRNA, accessed and retrieved from w.ncbi.nlm.nih.gov on May 4, 2021. (Year 2021).

NCBI Reference Sequence: NM_001 329798.2, *Homo sapiens* pleckstrin homology and RhoGEF domain containing G1 (PLEKHG1) transcript variant 1, mRNA, accessed and retrieved from www.ncbi.nlm.nih.gov on May 4, 2021. (Year: 2020).

NCBI Reference Sequence: NM_002505.5, *Homo sapiens* nuclear transcription factorY subunit alpha (NFYA), transcript variant 1, mRNA, accessed and retrieved from www.ncbi.nlm.nih.gov on May 4, 2021. (Year: 2021).

NCBI Reference Sequence: NM_030882.4, *Homo sapiens* apolipoprotein L2 (APOL2), transcript variant alpha, mRNA, accessed and retrieved from www.ncbi.nlm.nih.gov on May 4, 2021. (Year: 2021).

"BLOCK-iTTM Pol II miR RNAi Expression Vector Kits", User Manual, Version F, Invitrogen. (Year: 2010).

"Database GenBank: BC086489.1, Oct. 27, 2006 (4 pages)".

"Database GenBank: X60790.1, Jun. 26, 2016 (3 pages)".

"International Preliminary Report on Patentability corresponding to International Application No. PCT/US2017/050242 mailed Mar. 21, 2019".

"International Search Report and Written Opinion corresponding to International Application No. PCT/US2017/050242 mailed Dec. 21, 2017".

Ambros, Victor, "The functions of animal microRNAs", Nature 431:350-355 (Sep. 16, 2004).

Bartel, Davidp. , "MicroRNAs: genomics, biogenesis, mechanism, and function", Cell, 116(2), 2004, 281-297.

Bartel, Davidp. , "MicroRNAs: target recognition and regulatory functions", Cell, 136(2), 2009, 215-233.

Mccutcheon, et al., ""Expression of the splicing regulator polypyrimidine tract-binding protein in normal and neoplastic brain", Neuro-Oncology 6, 9-14 (2004)".

Mercer, et al., ""Long noncoding RNAs in neuronal-glial fate specification and oligodendrocyte lineage maturation", BMC Neuroscience 11(14):1-15. (2010)".

O'Brien, et al., "Overview of MicroRNA Biogenesis, Mechanisms of Actions, and Circulation", Frontiers in Endocrinology vol. 9, Article 402 (Aug. 2018) 12 pages.

Qian, et al., "Reversing a model of Parkinson's disease with in situ converted nigral neurons", Nature 582:550-556 (Jun. 25, 2000) 28 pages.

Xue, et al., ""Direct conversion of fibroblasts to neurons by reprogramming PTB-regulated micro RNA circuits", Cell 152:82-96 (2013)".

Xue, et al., ""Sequential regulatory loops as key gatekeepers for neuronal reprogramming in human cells, Nature Neuroscience", 19:807-815 (2016)".

"U.S. Appl. No. 17/542,150; office action mailed Jan. 24, 2025".

"U.S. Appl. No. 18/740,877; office action mailed Nov. 13, 2024".

U.S. Appl. No. 18/740,877; office action mailed Apr. 4, 2025.

"U.S. Appl. No. 17/542,150; office action mailed Nov. 17, 2025".

"U.S. Appl. No. 18/740,877; office action mailed Nov. 20, 2025".

"*Homo sapiens* polypyrimidine tract binding protein 1 (PTBP1 ), transcript variant 1, mRNA", NCBI Reference Sequence: NM_002819.2 accessed and retrieved from ncbi.nlm. nih.gov on Oct. 31, 2025 (2002) 5 pages.

"Rattus norvegicus polypyrimidine tract binding protein (Ptb), mRNA", NCBI Reference Sequence: NM_022516.1, accessed and retrieved from ncbi.nlm.nih.gov on Oct. 31, 2025 (2002) 4 pages.

"Thermo Scientific Dharmacon ON-TARGET plus siRNA", The Standard for siRNA Specificity, Thermo Fisher Scientific Inc. (2009) 8 pages.

Feng, et al., "RNA interference-produced autoregulation of inducible nitric oxide synthase expression", FEBS Letters 585:2488-2492 (Jul. 2011).

Gao, et al., "Inhibition of hepatitis B virus gene expression and replication by artificial microRNA", World Journal of Gastroenterology 14(29):4684-4689 (Aug. 7, 2008).

Liu, et al., "An artificial miRNA against HPSE suppresses melanoma invasion properties, correlating with a down-regulation of chemokines and MAPK phosphorylation", PLoS One 7(6):e38659 (Jun. 15, 2012) 12 pages.

Zhang, et al., "The effect of STAT3 and survivin silencing on the growth of human bladder carcinoma cells", Tumor Biology 35:5401-5407 (Feb. 12, 2014).

* cited by examiner

STRIATAL OLIG001-AAV-GFP + 10 DAYS

GFP/OLIG2          GFP/NEUN          GFP/GFAP

STRIATAL OLIG001-AAV-GFP + 6 MONTHS

GFP/OLIG2          GFP/NEUN          GFP/GFAP

AAV-4miRNA-GFP + 10-DAYS

AAV-4miRNA-GFP + 6 WEEKS

| GFP | NEUN | MERGE |
| --- | --- | --- |

| GFP | DARPP32 | MERGE |
| --- | --- | --- |

| GFP | PARVALBUMIN | MERGE |
| --- | --- | --- |

AAV-4miRNA + 6 MONTHS
NEUN          GFAP          OLIG2
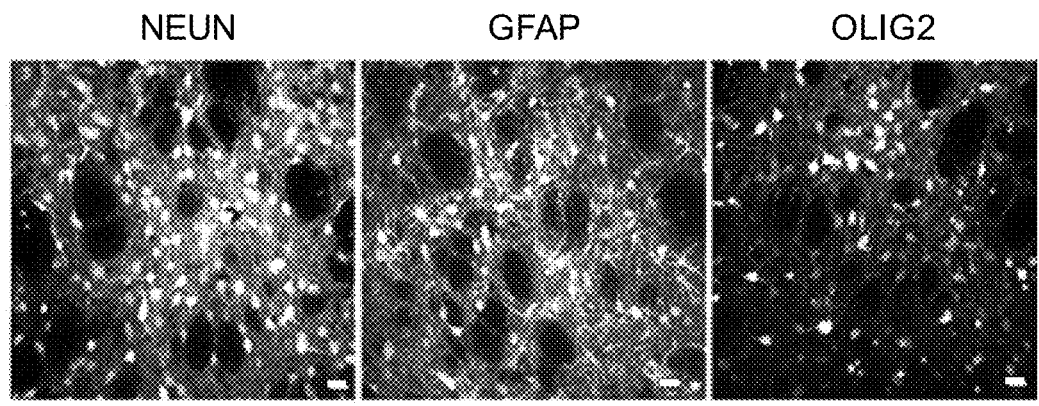
*FIG. 3C*
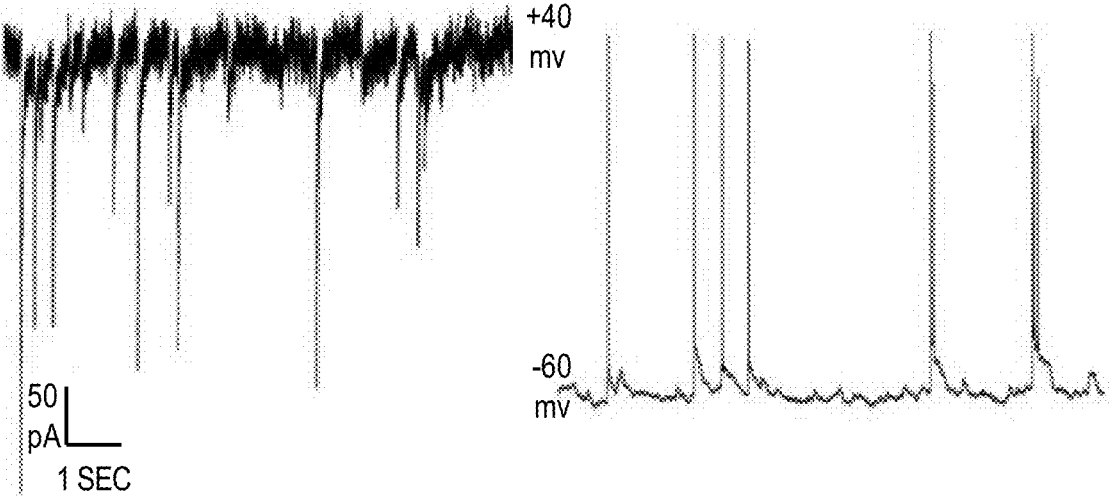
*FIG. 4A*                *FIG. 4B*

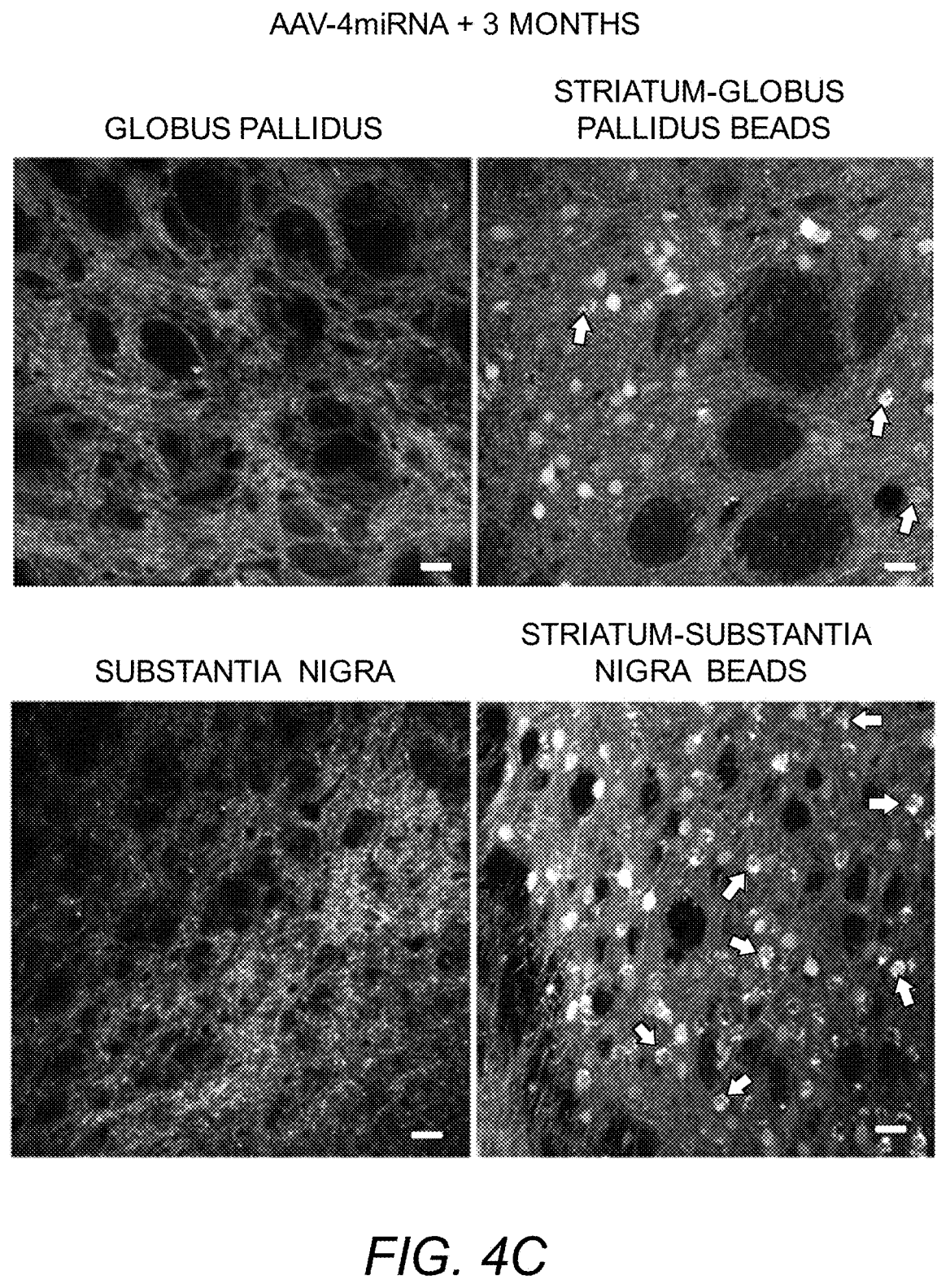

AAV-4miRNA + 3 MONTHS

GLOBUS PALLIDUS

STRIATUM-GLOBUS
PALLIDUS BEADS

SUBSTANTIA NIGRA

STRIATUM-SUBSTANTIA
NIGRA BEADS

*FIG. 4C*

GENERATION OF NEURONS BY REPROGRAMMING OF OLIGODENDROCYTES AND OLIGODENDROCYTE PRECURSOR CELLS

STATEMENT OF GOVERNMENT SUPPORT

This invention was made with government support under Grant No. NS082289 awarded by National Institutes of Health. The government has certain rights to this invention.

STATEMENT REGARDING ELECTRONIC FILING OF A SEQUENCE LISTING

A Sequence Listing in XML format, submitted under 37 C.F.R. § 1.821-1.834 entitled 5470-785CT2_ST26.xml, 14,778 bytes in size, generated on Jun. 6, 2024 and filed electronically, is provided in lieu of a paper copy. This Sequence Listing is hereby incorporated by reference into the specification for its disclosures.

FIELD OF THE INVENTION

The invention relates to products and methods for transdifferentiating oligodendrocytes and/or oligodendrocyte precursor cells to neurons. The invention further relates to methods of treating central nervous system disorders and conditions.

BACKGROUND OF THE INVENTION

With expanding knowledge of differentiation factors, it has become possible to reprogram resident cells in vivo (Heinrich et al., *Nat. Cell Biol.* 17:204 (2015)). For example, after cortical injury, the expression of NeuroDI reprogrammed reactive astrocytes into NeuN positive cells that fired action potentials and received synaptic input (Guo et al., *Cell Stem Cell* 14:188 (2014)). Similarly astrocytes have been converted into neurons in transgenic mice that expressed three conversion factors, Asc11, Brn2a and Myt11 (Torper et al., *Proc. Nat. Acad. Sci.* 110:7038 (2013)), while following injury NG2/olig2 positive cells could be transdifferentiated into neurons by the expression of SOX2 and Asc11 (Heinrich et al., *Stem Cell Reports* 3:1000 (2014)). These studies clearly established that at least in the context of injury, astrocytes and oligodendrocyte precursor cells (OPCs) can be induced to transdifferentiate into neurons in the central nervous system (CNS). However, this proof of principle involved either transgenic mice or retroviral mediated gene expression where, in the case of retroviral vectors, the potential for insertional mutagenesis precludes clinical consideration.

The present invention overcomes shortcomings in the art by providing products and methods for conversion of oligodendrocytes and/or oligodendrocyte precursor cells to functional neurons.

SUMMARY OF THE INVENTION

Given the potential to reprogram cells to neurons in the CNS, oligodendrocytes and oligodendrocyte precursor cells (OPCs) provide an excellent endogenous target cell population. Oligodendrocytes and OPCs comprise a substantial population in the CNS and in many neurological disorders, the OPC population expands in areas of neuropathology. For example, a significant increase in OPCs occurs in clinical samples from ALS patients (Kang et al., *Nat. Neurosci.*

16:571 (2013)) and in intractable pediatric epileptics (Sakuma et al., Neurosci. Lett. 566:188 (2014)). Clearly, in the context of neuropathology this CNS cell population provides a viable source for neuronal reprogramming.

The present invention is based, in part, on the development of vectors and methods for transdifferentiation of oligodendrocytes and/or OPCs into neurons. The approach relied upon two recent observations. Xue et al. (*Cell* 152:82 (2013)) reported that suppression of polypyrimidine-tract-binding (PTB) protein expression in cultured fibroblasts caused a portion of the fibroblasts to differentiate into functional neurons. Thus, manipulation of a single factor could induce neuronal reprogramming. Secondly, we recently developed a novel AAV vector where the chimeric capsid confers a dominant oligodendrocyte tropism in the rat striatum.

Thus, one aspect of the invention relates to a expression cassette comprising a polynucleotide encoding an antisense RNA or an interfering RNA targeted to a polynucleotide encoding a mammalian polypyrimidine tract binding protein 1 (PTBP1).

Another aspect of the invention relates to a virus particle comprising the expression cassette of the invention and a composition and pharmaceutical composition comprising the expression cassette or virus particle of the invention.

An additional aspect of the invention relates to a method of attenuating expression of PTBP1 in a cell, comprising contacting the cell with the expression cassette, virus particle, and/or composition of the invention, wherein the expression of PTBP1 is attenuated.

Another aspect of the invention relates to a method of transdifferentiating an oligodendrocyte or an oligodendrocyte precursor cell to a neuron, comprising contacting oligodendrocyte or oligodendrocyte precursor cell with the expression cassette, virus particle, and/or composition of the invention, thereby transdifferentiating the oligodendrocyte or oligodendrocyte precursor cell to a neuron.

A further aspect of the invention relates to a method of increasing the number of neurons in the brain of a mammalian subject, comprising delivering to the brain the expression cassette, virus particle, and/or composition of the invention, thereby increasing the number of neurons in the brain of the mammalian subject relative to the number of neurons prior to the delivery.

An additional aspect of the invention relates to a method of transdifferentiating an oligodendrocyte and/or a oligodendrocyte precursor cell to a neuron in the brain of a mammalian subject, comprising delivering to the brain the expression cassette, virus particle, and/or composition the invention, thereby transdifferentiating an oligodendrocyte and/or oligodendrocyte precursor cell to a neuron in the brain of the mammalian subject.

Another aspect of the invention relates to a method of treating a central nervous system disorder or condition responsive to an increase in the number of neurons in a mammalian subject in need thereof, the method comprising delivering to the brain the expression cassette, virus particle, and/or composition of the invention, thereby treating the central nervous system disorder or condition.

These and other aspects of the invention are set forth in more detail in the description of the invention below.

BRIEF DESCRIPTION OF THE DRAWINGS

FIGS. 3A-3C show the progression of oligodendrocyte transdifferentiation following Olig001AAV-4miRNA-GFP transduction in the rat striatum. (3A) Confocal images show that 10 days after Olig001AAV-4miRNA-GFP transduction, the vast majority of the GFP positive cells exhibit a typical oligodendrocyte morphology including GFP positive myelin in the striatal patches. Many GFP positive cells co-localize with Olig2 but do not co-localize with NeuN. This pattern was present throughout the area of striatal transduction, in all animals (n=4). (3B) By 6 weeks post transduction, confocal images show that most of the GFP positive cells co-localize with NeuN as well as subclasses of striatal GABAergic cells, such as DARPP32 and parvalbumin (arrows). NeuN/GFP co-localization was present throughout the area of transduction in all animals (n=5). (3C) Confocal images show that this neuronal pattern remains 6 months after vector transduction where GFP positive cells co-localize with NeuN but not GFAP or Olig2 (n=4). (Horizontal bars=20 microns).

FIGS. 4A-4C show electrophysiological and neuroanatomical evidence that the transdifferentiated oligodendrocytes become functional striatal neurons. (4A) A voltage clamp recording from a representative GFP fluorescent striatal cell shows action-potentials typical of a neuron. (4B) A current-clamp recording shows spontaneous post-synaptic potentials from the cell shown in (4A), indicative of synaptic input to the GFP positive cell. (4C) Confocal images show that 3 months after Olig001 AAV-4miRNA-GFP transduction, GFP positive nerve terminals are present in both the globus pallidus and the substantia nigra. Further, when fluorescent latex beads (0.04 μm) are infused into either the globus pallidus or substantia nigra 3 months after striatal transduction by OLIG001AAV-4miRNA-GFP, 2 weeks later the fluorescent beads have been retrogradely transported into GFP positive cell bodies in the ipsilateral striatum (white arrows). (Horizontal bars=20 microns).

DETAILED DESCRIPTION OF THE INVENTION

Figure 1A:
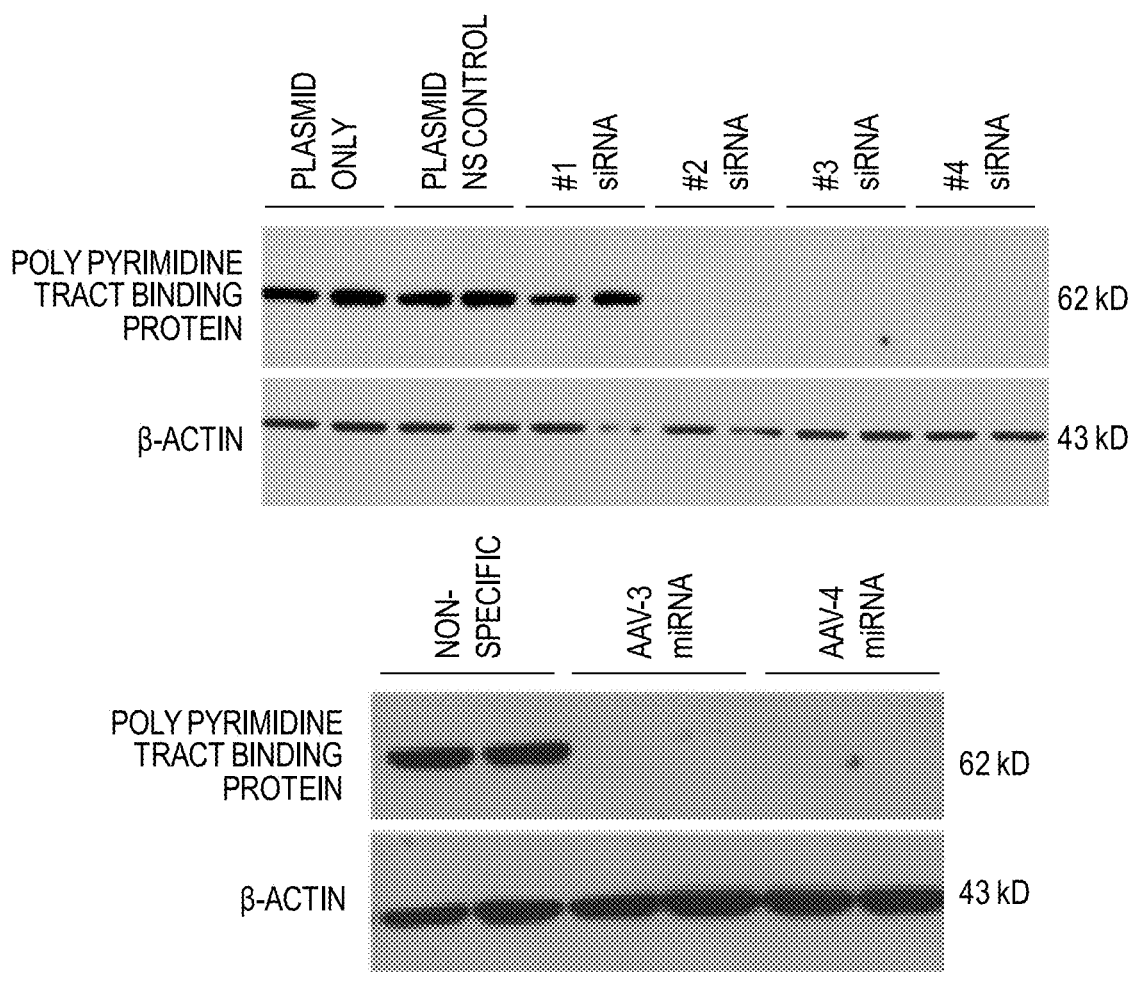
FIGS. 1A-1C show in vitro reduction of PTBP1 by siRNAs and miRNAs and long term selectivity of the Olig001 AAV vector in the rat striatum. (1A) The first western blot shows that numbers 3 and 4 siRNA completely prevented PTBP1 expression following transfection of HeLa cells with the siRNA and a rat ptbp expression plasmid. The second western blot shows that conversion of numbers 3 and 4 to miRNA packaged in AAV2 virus prevented PTBP1 expression in HEK293 cells. (1B) The oligodendrocyte preference for the Olig001 AAV-GFP vector in the rat striatum 10 days post-transduction is shown. GFP positive cells co-localized with Olig2 positive cells but did not co-localize with NeuN or GFAP positive cells. (1C) The same transduction pattern from the Olig001-AAV-GFP vector 6 months after striatal transduction in the rat is shown.

The present invention is based on the development of products and methods for transdifferentiating oligodendrocytes into functional neurons. The methods can be used to treat central nervous system disorders and conditions.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for production of recombinant and synthetic polypeptides, antibodies or antigen-binding fragments thereof, manipulation of nucleic acid sequences, production of transformed cells, the construction of rAAV constructs, modified capsid proteins, packaging vectors expressing the AAV rep and/or cap sequences, and transiently and stably transfected packaging cells. Such techniques are known to those skilled in the art. See, e.g., SAMBROOK et al., MOLECULAR CLONING: A LABORATORY MANUAL 2nd Ed. (Cold Spring Harbor, NY, 1989); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, nucleotide sequences, amino acid sequences and other references mentioned herein are incorporated by reference in their entirety.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

The term "consisting essentially of" as used herein in connection with a nucleic acid, protein or capsid structure means that the nucleic acid, protein or capsid structure does not contain any element other than the recited element(s) that significantly alters (e.g., more than about 1%, 5% or 10%) the function of interest of the nucleic acid, protein or capsid structure, e.g., tropism profile of the protein or capsid or a protein or capsid encoded by the nucleic acid.

The term "adeno-associated virus" (AAV) in the context of the present invention includes without limitation AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, and ovine AAV and any other AAV now known or later discovered. See, e.g., BERNARD N. FIELDS et al., VIROLOGY, volume 2, chapter 69 (4th ed., Lippincott-Raven Publishers). A number of additional AAV serotypes and clades have been identified (see, e.g., Gao et al., (2004) J. Virol. 78:6381-6388 and Table 1), which are also encompassed by the term "AAV."

The genomic sequences of various AAV and autonomous parvoviruses, as well as the sequences of the inverted terminal repeats (ITRs), Rep proteins, and capsid subunits are known in the art. Such sequences may be found in the literature or in public databases such as the GenBank® database. See, e.g., GenBank® Accession Numbers NC 002077, NC 001401, NC 001729, NC 001863, NC 001829, NC 001862, NC 000883, NC 001701, NC 001510, AF063497, U89790, AF043303, AF028705, AF028704, J02275, J01901, J02275, X01457, AF288061, AH009962, AY028226, AY028223, NC 001358, NC 001540, AF513851, AF513852, AY530579, AY631965, AY631966; the disclosures of which are incorporated herein in their entirety. See also, e.g., Srivistava et al., (1983) J. Virol. 45:555; Chiorini et al., (1998) J. Virol. 71:6823; Chiorini et al., (1999) J. Virol. 73:1309; Bantel-Schaal et al., (1999) J. Virol. 73:939; Xiao et al., (1999) J. Virol. 73:3994; Muramatsu et al., (1996) Virology 221:208; Shade et al., (1986) J. Virol. 58:921; Gao et al., (2002) Proc. Nat. Acad. Sci. USA 99:11854; international patent publications WO 00/28061, WO 99/61601, WO 98/11244; U.S. Pat. No. 6,156,303; the disclosures of which are incorporated herein in their entirety. See also Table 1. An early description of the AAV1, AAV2 and AAV3 terminal repeat sequences is provided by Xiao, X., (1996), "Characterization of Adeno-associated virus (AAV) DNA replication and integration," Ph.D. Dissertation, University of Pittsburgh, Pittsburgh, PA (incorporated herein it its entirety).

A "chimeric" AAV nucleic acid capsid coding sequence or AAV capsid protein is one that combines portions of two or more capsid sequences. A "chimeric" AAV virion or particle comprises a chimeric AAV capsid protein.

6

TABLE 1

| | GenBank Accession Number |
|---|---|
| Complete Genomes | |
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |
| Avian AAV strain DA-1 | NC_006263, AY629583 |
| Bovine AAV | NC_005889, AY388617 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530585 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |

7

TABLE 1-continued

| | GenBank Accession Number |
|---|---|
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| Hu14 (AAV9) | AY530579 |
| Hu31 | AY530596 |
| Hu32 | AY530597 |
| Clonal isolate | |
| AAV5 | Y18065, AF085716 |
| AAV 3 | NC_001729 |
| AAV 3B | NC_001863 |
| AAV4 | NC_001829 |
| Rh34 | AY243001 |
| Rh33 | AY243002 |
| Rh32 | AY243003 |

The term "tropism" as used herein refers to preferential entry of the virus into certain cell or tissue type(s) and/or preferential interaction with the cell surface that facilitates entry into certain cell or tissue types, optionally and preferably followed by expression (e.g., transcription and, optionally, translation) of sequences carried by the viral genome in the cell, e.g., for a recombinant virus, expression of the heterologous nucleotide sequence(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of a rAAV genome, gene expression from the viral genome may be from a stably integrated provirus and/or from a non-integrated episome, as well as any other form which the virus nucleic acid may take within the cell.

The term "tropism profile" refers to the pattern of transduction of one or more target cells, tissues and/or organs. Representative examples of chimeric AAV capsids have a tropism profile characterized by efficient transduction of oligodendrocytes with only low transduction of neurons, astrocytes, and other CNS cells.

The terms "specific for oligodendrocytes and or OPCs" and "has a tropism for oligodendrocytes and/or OPCs" as used herein refer to a viral vector that, when administered directly into the CNS, preferentially transduces oligodendrocytes and/or OPCs over neurons, astrocytes, and other CNS cell types. In some embodiments, at least about 80% of the transduced cells are oligodendrocytes and/or OPCs, e.g., at least about 85%, 90%, 95%, 96%, 97%, 98%, 99% or more are oligodendrocytes and/or OPCs.

The term "central nervous system (CNS) disorder or condition responsive to an increase in the number of neurons" as used herein refers to a disease, disorder, condition, or injury in which CNS cells are damaged, lost, or function improperly and which show an improvement in at least one symptom when the number of neurons in the CNS (e.g., at the site of tissue damage) is increased. The term includes diseases, disorders, conditions, and injuries in which CNS cells are directly affected as well as diseases, disorders, conditions, and injuries in which CNS cells become dysfunctional secondary to damage to other cells, tissues, or organs.

As used herein, "transduction" of a cell by a virus vector (e.g., an AAV vector) means entry of the vector into the cell and transfer of genetic material into the cell by the incorporation of nucleic acid into the virus vector and subsequent transfer into the cell via the virus vector.

Unless indicated otherwise, "efficient transduction" or "efficient tropism," or similar terms, can be determined by reference to a suitable positive or negative control (e.g., at least about 50%, 60%, 70%, 80%, 85%, 90%, 95% or more of the transduction or tropism, respectively, of a positive control or at least about 110%, 120%, 150%, 200%, 300%, 500%, 1000% or more of the transduction or tropism, respectively, of a negative control).

Similarly, it can be determined if a virus "does not efficiently transduce" or "does not have efficient tropism" for a target tissue, or similar terms, by reference to a suitable control. In particular embodiments, the virus vector does not efficiently transduce (i.e., does not have efficient tropism for) liver, kidney, gonads and/or germ cells. In particular embodiments, undesirable transduction of tissue(s) (e.g., liver) is 20% or less, 10% or less, 5% or less, 1% or less, 0.1% or less of the level of transduction of the desired target tissue(s) (e.g., oligodendrocytes).

As used herein, the term "polypeptide" encompasses both peptides and proteins, unless indicated otherwise.

A "nucleic acid" or "nucleotide sequence" is a sequence of nucleotide bases, and may be RNA, DNA or DNA-RNA hybrid sequences (including both naturally occurring and non-naturally occurring nucleotide), but is preferably either single or double stranded DNA sequences.

As used herein, an "isolated" nucleic acid or nucleotide sequence (e.g., an "isolated DNA" or an "isolated RNA") means a nucleic acid or nucleotide sequence separated or substantially free from at least some of the other components of the naturally occurring organism or virus, for example, the cell or viral structural components or other polypeptides or nucleic acids commonly found associated with the nucleic acid or nucleotide sequence.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

By the term "treat," "treating," or "treatment of" (or grammatically equivalent terms) it is meant that the severity of the subject's condition is reduced or at least partially improved or ameliorated and/or that some alleviation, mitigation or decrease in at least one clinical symptom is achieved and/or there is a delay in the progression of the condition and/or prevention or delay of the onset of a disease or disorder. The term "treat," "treats," "treating," or "treatment of" and the like also include prophylactic treatment of the subject (e.g., to prevent the onset of infection or cancer or a disorder). As used herein, the term "prevent," "prevents," or "prevention" (and grammatical equivalents thereof) are not meant to imply complete abolition of disease and encompasses any type of prophylactic treatment that reduces the incidence of the condition, delays the onset and/or progression of the condition, and/or reduces the symptoms associated with the condition. Thus, unless the context indicates otherwise, the term "treat," "treating," or "treatment of" (or grammatically equivalent terms) refer to both prophylactic and therapeutic regimens.

An "effective" or "therapeutically effective" amount as used herein is an amount that is sufficient to provide some improvement or benefit to the subject. Alternatively stated, an "effective" or "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

A "heterologous nucleotide sequence" or "heterologous nucleic acid" is a sequence that is not naturally occurring in the virus. Generally, the heterologous nucleic acid or nucleotide sequence comprises an open reading frame that encodes a polypeptide and/or a nontranslated RNA.

A "therapeutic polypeptide" can be a polypeptide that can alleviate or reduce symptoms that result from an absence or defect in a protein in a cell or subject. In addition, a "therapeutic polypeptide" can be a polypeptide that otherwise confers a benefit to a subject, e.g., anti-cancer effects or improvement in transplant survivability.

As used herein, the term "vector," "virus vector," "delivery vector" (and similar terms) generally refers to a virus particle that functions as a nucleic acid delivery vehicle, and which comprises the viral nucleic acid (i.e., the vector genome) packaged within the virion. Virus vectors according to the present invention can package an AAV or rAAV genome or any other nucleic acid including viral nucleic acids. Alternatively, in some contexts, the term "vector," "virus vector," "delivery vector" (and similar terms) may be used to refer to the vector genome (e.g., vDNA) in the absence of the virion and/or to a viral capsid that acts as a transporter to deliver molecules tethered to the capsid or packaged within the capsid.

A "recombinant AAV vector genome" or "rAAV genome" is an AAV genome (i.e., vDNA) that comprises at least one inverted terminal repeat (e.g., one, two or three inverted terminal repeats) and one or more heterologous nucleotide sequences. rAAV vectors generally retain the 145 base terminal repeat(s) (TR(s)) in cis to generate virus; however, modified AAV TRs and non-AAV TRs including partially or completely synthetic sequences can also serve this purpose. All other viral sequences are dispensable and may be supplied in trans (Muzyczka, (1992) *Curr. Topics Microbiol. Immunol.* 158:97). The rAAV vector optionally comprises two TRs (e.g., AAV TRs), which generally will be at the 5' and 3' ends of the heterologous nucleotide sequence(s), but need not be contiguous thereto. The TRs can be the same or different from each other. The vector genome can also contain a single ITR at its 3' or 5' end.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or the SV40 hairpin that serves as the origin of SV40 replication can be used as a TR, which can further be modified by truncation, substitution, deletion, insertion and/or addition. Further, the TR can be partially or completely synthetic, such as the "double-D sequence" as described in U.S. Pat. No. 5,478,745 to Samulski et al.

An "AAV inverted terminal repeat" or "AAV ITR" may be from any AAV, including but not limited to serotypes 1, 2, 3, 4, 5, 6, 7, 8, 9, 10 or 11 or any other AAV now known or later discovered (see, e.g., Table 1). An AAV ITR need not have the native terminal repeat sequence (e.g., a native AAV ITR sequence may be altered by insertion, deletion, truncation and/or missense mutations), as long as the terminal repeat mediates the desired functions, e.g., replication, virus packaging, integration, and/or provirus rescue, and the like.

The virus vectors of the invention can further be "targeted" virus vectors (e.g., having a directed tropism) and/or a "hybrid" parvovirus (i.e., in which the viral ITRs and viral capsid are from different parvoviruses) as described in international patent publication WO 00/28004 and Chao et al., (2000) *Mol. Therapy* 2:619.

Further, the viral capsid or genomic elements can contain other modifications, including insertions, deletions and/or substitutions.

The term "template" or "substrate" is used herein to refer to a polynucleotide sequence that may be replicated to produce the parvovirus viral DNA. For the purpose of vector production, the template will typically be embedded within a larger nucleotide sequence or construct, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like). Alternatively, the template may be stably incorporated into the chromosome of a packaging cell.

As used herein, parvovirus or AAV "Rep coding sequences" indicate the nucleic acid sequences that encode the parvoviral or AAV non-structural proteins that mediate viral replication and the production of new virus particles. The parvovirus and AAV replication genes and proteins have been described in, e.g., FIELDS et al., VIROLOGY, volume 2, chapters 69 & 70 (4th ed., Lippincott-Raven Publishers).

The "Rep coding sequences" need not encode all of the parvoviral or AAV Rep proteins. For example, with respect to AAV, the Rep coding sequences do not need to encode all four AAV Rep proteins (Rep78, Rep 68, Rep52 and Rep40), in fact, it is believed that AAV5 only expresses the spliced Rep68 and Rep40 proteins. In representative embodiments, the Rep coding sequences encode at least those replication proteins that are necessary for viral genome replication and packaging into new virions. The Rep coding sequences will generally encode at least one large Rep protein (i.e., Rep78/68) and one small Rep protein (i.e., Rep52/40). In particular embodiments, the Rep coding sequences encode the AAV Rep78 protein and the AAV Rep52 and/or Rep40 proteins. In other embodiments, the Rep coding sequences encode the Rep68 and the Rep52 and/or Rep40 proteins. In a still further embodiment, the Rep coding sequences encode the Rep68 and Rep52 proteins, Rep68 and Rep40 proteins, Rep78 and Rep52 proteins, or Rep78 and Rep40 proteins.

As used herein, the term "large Rep protein" refers to Rep68 and/or Rep78. Large Rep proteins of the claimed invention may be either wild-type or synthetic. A wild-type large Rep protein may be from any parvovirus or AAV, including but not limited to serotypes 1, 2, 3a, 3b, 4, 5, 6, 7, 8, 9, 10, 11, or 13, or any other AAV now known or later discovered (see, e.g., Table 1). A synthetic large Rep protein may be altered by insertion, deletion, truncation and/or missense mutations.

Those skilled in the art will further appreciate that it is not necessary that the replication proteins be encoded by the same polynucleotide. For example, for MVM, the NS-1 and NS-2 proteins (which are splice variants) may be expressed independently of one another. Likewise, for AAV, the p19 promoter may be inactivated and the large Rep protein(s) expressed from one polynucleotide and the small Rep protein(s) expressed from a different polynucleotide. Typically, however, it will be more convenient to express the replication proteins from a single construct. In some systems, the viral promoters (e.g., AAV p19 promoter) may not be recognized by the cell, and it is therefore necessary to express the large and small Rep proteins from separate expression cassettes. In other instances, it may be desirable to express the large Rep and small Rep proteins separately, i.e., under the control of separate transcriptional and/or translational control elements. For example, it may be desirable to control expression of the large Rep proteins, so as to decrease the ratio of large to small Rep proteins. In the case of insect cells, it may be advantageous to down-regulate expression of the large Rep proteins (e.g., Rep78/68) to avoid toxicity to the cells (see, e.g., Urabe et al., (2002) *Human Gene Therapy* 13:1935).

As used herein, the parvovirus or AAV "cap coding sequences" encode the structural proteins that form a functional parvovirus or AAV capsid (i.e., can package DNA and infect target cells). Typically, the cap coding sequences will encode all of the parvovirus or AAV capsid subunits, but less than all of the capsid subunits may be encoded as long as a functional capsid is produced. Typically, but not necessarily, the cap coding sequences will be present on a single nucleic acid molecule.

The terms "rAAV particle" and "rAAV virion" are used interchangeably here. A "rAAV particle" or "rAAV virion" comprises a rAAV vector genome packaged within an AAV capsid.

The AAV capsid structure is described in more detail in BERNARD N. FIELDS et al., VIROLOGY, volume 2, chapters 69 & 70 (4th ed., Lippincott-Raven Publishers).

By "substantially retain" a property, it is meant that at least about 75%, 85%, 90%, 95%, 97%, 98%, 99% or 100% of the property (e.g., activity or other measurable characteristic) is retained.

The terms "transdifferentiation," "transdifferentiating," and transdifferentiate" as used herein refer to the conversion of one cell type to another cell type. The transdifferentiation can be confirmed by the loss of markers of the first cell type and gain of markers of the second cell type.

The term "differentiation factor" as used herein, refers to a compound, molecule, or polypeptide that promotes the differentiation of a cell from one cell type or stage to another.

The term "antisense nucleotide sequence" or "antisense oligonucleotide" as used herein, refers to a nucleotide sequence that is complementary to a specified DNA or RNA sequence. Antisense oligonucleotides and nucleic acids that express the same can be made in accordance with conventional techniques. See, e.g., U.S. Pat. No. 5,023,243 to Tullis; U.S. Pat. No. 5,149,797 to Pederson et al. The antisense nucleotide sequence can be complementary to the entire nucleotide sequence encoding the polypeptide or a portion thereof of at least 10, 15, 20, 25, 30, 35, 40, 45, 50, 75, 100, 150, 200, 300, or 500 contiguous bases or less than 500, 300, 200, 150, 100, 75, 50, 45, 40, 35, 30, 25, 20, 15, or 10 contiguous bases and will reduce the level of polypeptide production.

Those skilled in the art will appreciate that it is not necessary that the antisense nucleotide sequence be fully complementary to the target sequence as long as the degree of sequence similarity is sufficient for the antisense nucleotide sequence to hybridize to its target and reduce production of the polypeptide. As is known in the art, a higher degree of sequence similarity is generally required for short antisense nucleotide sequences, whereas a greater degree of mismatched bases will be tolerated by longer antisense nucleotide sequences.

For example, hybridization of such nucleotide sequences can be carried out under conditions of reduced stringency, medium stringency or even stringent conditions (e.g., conditions represented by a wash stringency of 35-40% formamide with 5×Denhardt's solution, 0.5% SDS and 1×SSPE at 37° C.; conditions represented by a wash stringency of 40-45% formamide with 5×Denhardt's solution, 0.5% SDS, and 1×SSPE at 42° C.; and/or conditions represented by a wash stringency of 50% formamide with 5×Denhardt's solution, 0.5% SDS and 1×SSPE at 42° C., respectively) to the nucleotide sequences specifically disclosed herein. See, e.g., Sambrook et al., Molecular Cloning: A Laboratory Manual 2nd Ed. (Cold Spring Harbor, NY, 1989).

In other embodiments, antisense nucleotide sequences of the invention have at least about 70%, 80%, 90%, 95%, 97%, 98% or higher sequence similarity with the complement of the coding sequences specifically disclosed herein and will reduce the level of polypeptide production.

The length of the antisense nucleotide sequence (i.e., the number of nucleotides therein) is not critical as long as it binds selectively to the intended location and reduces transcription and/or translation of the target sequence, and can be determined in accordance with routine procedures. In general, the antisense nucleotide sequence will be from about eight, ten or twelve nucleotides in length up to about 20, 30, 50, 75 or 100 nucleotides, or longer, in length.

An antisense nucleotide sequence can be constructed using chemical synthesis and enzymatic ligation reactions by procedures known in the art. For example, an antisense nucleotide sequence can be chemically synthesized using naturally occurring nucleotides or various modified nucleotides designed to increase the biological stability of the molecules or to increase the physical stability of the duplex formed between the antisense and sense nucleotide sequences, e.g., phosphorothioate derivatives and acridine substituted nucleotides can be used. Examples of modified nucleotides which can be used to generate the antisense nucleotide sequence include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomet-hyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopenten-yladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleotide sequence can be produced using an expression vector into which a nucleic acid has been cloned in an antisense orientation (i.e., RNA transcribed from the inserted nucleic acid will be of an antisense orientation to a target nucleic acid of interest).

The antisense nucleotide sequences of the invention further include nucleotide sequences wherein at least one, or all, of the internucleotide bridging phosphate residues are modified phosphates, such as methyl phosphonates, methyl phosphonothioates, phosphoromorpholidates, phosphoropiperazidates and phosphoramidates. For example, every other one of the internucleotide bridging phosphate residues can be modified as described. In another non-limiting example, the antisense nucleotide sequence is a nucleotide sequence in which one, or all, of the nucleotides contain a 2' lower alkyl moiety (e.g., $C_1$-$C_4$, linear or branched, saturated or unsaturated alkyl, such as methyl, ethyl, ethenyl, propyl, 1-propenyl, 2-propenyl, and isopropyl). For example, every other one of the nucleotides can be modified as described. See also, Furdon et al., *Nucleic Acids Res.* 17:9193 (1989); Agrawal et al., *Proc. Natl. Acad. Sci. USA* 87:1401 (1990); Baker et al., *Nucleic Acids Res.* 18:3537 (1990); Sproat et al., *Nucleic Acids Res.* 17:3373 (1989); Walder and Walder, *Proc. Natl. Acad. Sci. USA* 85:5011 (1988); incorporated by reference herein in their entireties for their teaching of methods of making antisense molecules, including those containing modified nucleotide bases).

As used herein, "RNAi" or "RNA interference" refers to the process of sequence-specific post-transcriptional gene silencing, mediated by an interfering RNA which is a double-stranded RNA (dsRNA). As used herein, "dsRNA" refers to RNA that is partially or completely double stranded. Examples of double stranded RNA useful in RNA interference include small interfering RNA (siRNA), small interfering nucleic acid (siNA), short hairpin RNA (shRNA), microRNA (miRNA), and the like. In the RNAi process, dsRNA comprising a first (antisense) strand that is complementary to a portion of a target gene and a second (sense) strand that is fully or partially complementary to the first antisense strand is introduced into a cell or organism.

RNAi begins with the cleavage of longer dsRNAs into small interfering RNAs (siRNAs) by an RNascIII-like enzyme, dicer. SiRNAs are dsRNAs that are usually about 19 to about 28 nucleotides, or about 20 to about 25 nucleotides, or about 21 to about 22 nucleotides in length and often contain 2-nucleotide 3' overhangs, and 5' phosphate and 3' hydroxyl termini. One strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. Therefore, the siRNA strand that is incorporated into RISC is known as the guide strand or the antisense strand. The other siRNA strand, known as the passenger strand or the sense strand, is eliminated from the siRNA and is at least partially homologous to the target mRNA. Those of skill in the art will recognize that, in principle, either strand of an siRNA can be incorporated into RISC and function as a guide strand. However, siRNA design (e.g., decreased siRNA duplex stability at the 5' end of the antisense strand) can favor incorporation of the antisense strand into RISC.

RISC-mediated cleavage of mRNAs having a sequence at least partially complementary to the guide strand leads to a decrease in the steady state level of that mRNA and of the corresponding protein encoded by this mRNA. Alternatively, RISC can also decrease expression of the corresponding protein via translational repression without cleavage of the target mRNA. Other RNA molecules and RNA-like molecules can also interact with RISC and silence gene expression. Examples of other RNA molecules that can interact with RISC include shRNAs, single-stranded siRNAs, miRNAs, and dicer-substrate 27-mer duplexes. The term "interfering RNAs" as used herein refers to a double-stranded interfering RNA unless otherwise noted. Examples of RNA-like molecules that can interact with RISC include RNA molecules containing one or more chemically modified nucleotides, one or more deoxyribonucleotides, and/or one or more non-phosphodiester linkages. For purposes of the present discussion, all RNA or RNA-like molecules that can interact with RISC and participate in RISC-mediated changes in gene expression will be referred to as "interfering RNAs." SiRNAs, shRNAs, miRNAs, and dicer-substrate 27-mer duplexes are, therefore, subsets of "interfering RNAs."

MicroRNAs (miRNAs) are non-protein coding RNAs, generally of between about 18 to about 25 nucleotides in length (commonly about 20-24 nucleotides in length in plants). These miRNAs direct cleavage in trans of target transcripts, negatively regulating the expression of genes involved in various regulation and development pathways (Bartel, *Cell* 116:281 (2004); Zhang et al., *Dev. Biol.* 289:3 (2006)).

Genes encoding miRNAs yield primary miRNAs (termed a "pri-miRNA") of 70 to 300 bp in length that can form imperfect stem-loop structures. A single pri-miRNA may contain from one to several miRNA precursors. In animals, pri-miRNAs are processed in the nucleus into shorter hairpin RNAs of about 65 nt (pre-miRNAs) by the RNaseIII enzyme Drosha and its cofactor DGCR8/Pasha. The pre-miRNA is then exported to the cytoplasm, where it is further processed by another RNaseIII enzyme, Dicer, releasing a miRNA/miRNA* duplex of about 22 nt in size. Many reviews on microRNA biogenesis and function are available, for example, see, Bartel, *Cell* 116:281 (2004), Murchison et al., *Curr. Opin. Cell Biol.* 16:223 (2004), Dugas et al., *Curr. Opin. Plant Biol.* 7:512 (2004) and Kim, *Nature Rev. Mol. Cell Biol.* 6:376 (2005).

As used herein, the terms "amount sufficient to inhibit expression" and "amount sufficient to attenuate expression" refers to a concentration or amount of the interfering RNA that is sufficient to reduce levels or stability of mRNA or protein produced from the PTBP1 gene in a cell. As used herein, "inhibiting expression" and "attenuating expression" refer to the absence or observable decrease in the level of protein and/or mRNA product from the PTBP1 gene.

As used herein, "complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. For example, the sequence "A-G-T" binds to the complementary sequence "T-C-A." It is understood that two polynucleotides may hybridize to each other even if they are not completely complementary to each other, provided that each has at least one region that is substantially complementary to the other.

The terms "complementary" or "complementarity," as used herein, refer to the natural binding of polynucleotides under permissive salt and temperature conditions by base-pairing. Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

As used herein, the terms "substantially complementary" or "partially complementary" mean that two nucleic acid sequences are complementary at least at about 80% of their nucleotides. In some embodiments, the two nucleic acid sequences can be complementary at least at 85%, 90%, 95%, 96%, 97%, 98%, 99% or more of their nucleotides. The terms "substantially complementary" and "partially complementary" can also mean that two nucleic acid sequences can hybridize under high stringency conditions and such conditions are well known in the art.

As used herein, the terms "contacting," "introducing," "delivering," and "administering" are used interchangeably, and refer to a process by which antisense RNA or interfering RNA of the present invention or a nucleic acid molecule encoding an antisense RNA or an interfering RNA of this invention is delivered to a cell or a subject, in order to inhibit or alter or modify expression of PTBP1 in the cell or subject. The antisense RNA or interfering RNA may be administered in a number of ways, including, but not limited to, direct introduction into a cell (i.e., intracellularly) and/or extracellular introduction into a cavity, interstitial space, regional circulation feeding a particular organ or tissue, or into a tissue or structure (e.g., the striatum).

"Introducing" in the context of a cell or a subject means presenting the nucleic acid molecule to the cell or subject in such a manner that the nucleic acid molecule gains access to the interior of a cell. Where more than one nucleic acid molecule is to be introduced these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into cells in a single transformation event or in separate transformation events. Thus, the term "transformation" as used herein refers to the introduction of a heterologous nucleic acid into a cell. Transformation of a cell may be stable or transient.

Embodiments of the invention are directed to expression cassettes designed to express the nucleic acids of the present invention. As used herein, "expression cassette" means a nucleic acid molecule having at least a control sequence operably linked to a nucleotide sequence of interest. In this manner, for example, promoters in operable interaction with the nucleotide sequences for the antisense RNAs or interfering RNAs of the invention are provided in expression cassettes for expression in a cell.

As used herein, the term "promoter" refers to a region of a nucleotide sequence that incorporates the necessary signals for the efficient expression of a coding sequence. This may include sequences to which an RNA polymerase binds, but is not limited to such sequences and can include regions to which other regulatory proteins bind together with regions involved in the control of protein translation and can also include coding sequences.

Furthermore, a "promoter" of this invention is a promoter capable of initiating transcription in a cell. Such promoters include those that drive expression of a nucleotide sequence constitutively, those that drive expression when induced, and those that drive expression in a tissue- or developmentally-specific manner, as these various types of promoters are known in the art.

For purposes of the invention, the regulatory regions (i.e., promoters, transcriptional regulatory regions, and translational termination regions) can be native/analogous to the cell and/or the regulatory regions can be native/analogous to the other regulatory regions. Alternatively, the regulatory regions may be heterologous to the cell and/or to each other (i.e., the regulatory regions). Thus, for example, a promoter can be heterologous when it is operably linked to a polynucleotide from a species different from the species from which the polynucleotide was derived. Alternatively, a promoter can also be heterologous to a selected nucleotide sequence if the promoter is from the same/analogous species from which the polynucleotide is derived, but one or both (i.e., promoter and polynucleotide) are substantially modified from their original form and/or genomic locus, or the promoter is not the native promoter for the operably linked polynucleotide.

The choice of promoters to be used depends upon several factors, including, but not limited to, cell- or tissue-specific expression, desired expression level, efficiency, inducibility and selectability. For example, where expression in a specific tissue or organ is desired, a tissue-specific or tumor-specific promoter can be used (e.g., a breast cancer specific promoter). In contrast, where expression in response to a stimulus is desired, an inducible promoter can be used. Where continuous expression is desired throughout the cells of a subject, a constitutive promoter can be used. It is a routine matter for one of skill in the art to modulate the expression of a nucleotide sequence by appropriately selecting and positioning promoters and other regulatory regions relative to that sequence.

Therefore, in some instances, constitutive promoters can be used. Examples of constitutive promoters include, but are not limited to, pol III promoters, such as the U6 or HI promoters, or pol II promoters, such as the cytomegalovirus promoter and the SV40-derived initial promoter, and mammalian constitutive protein gene promoters such as the β-actin gene promoter, the tRNA promoter, and the like. In some embodiments, the constitutive promoter is a hybrid chicken beta actin promoter or a truncated version thereof (CBh, Gray et al., *Human Gene Ther.* 22:1143 (2011)).

Moreover, tissue-specific regulated nucleic acids and/or promoters as well as tumor-specific regulated nucleic acids and/or promoters have been reported. Thus, in some embodiments, tissue-specific or tumor-specific promoters can be used. Some reported tissue-specific nucleic acids include, without limitation, B29 (B cells), CD14 (monocytic cells), CD43 (leukocytes and platelets), CD45 (hematopoietic cells), CD68 (macrophages), desmin (muscle), elastase-1 (pancreatic acinar cells), endoglin (endothelial cells), fibronectin (differentiating cells and healing tissues), FLT-1 (endothelial cells), GFAP (astrocytes), GPIIb (megakaryocytes), ICAM-2 (endothelial cells), INF-β (hematopoietic cells), Mb (muscle), NPHSI (podocytes), OG-2 (osteoblasts), SP-B (lungs), SYN1 (neurons), and WASP (hematopoietic cells). Some reported tumor-specific nucleic acids and promoters include, without limitation, AFP (hepatocellular carcinoma), CCKAR (pancreatic cancer), CEA (epithelial cancer), c-crbB2 (breast and pancreatic cancer), COX-2, CXCR4, E2F-1, HE4, LP, MUC1 (carcinoma), PRC1 (breast cancer), PSA (prostate cancer), RRM2 (breast cancer), survivin, TRP1 (melanoma), and TYR (melanoma).

In some instances, inducible promoters can be used. Examples of inducible promoters include, but are not limited to, tetracycline repressor system promoters, Lac repressor system promoters, copper-inducible system promoters, salicylate-inducible system promoters (e.g., the PR1a system), glucocorticoid-inducible promoters, and ecdysone-inducible system promoters.

In addition to the promoters described above, the expression cassette also can include other regulatory sequences. As used herein, "regulatory sequences" means nucleotide sequences located upstream (5' non-coding sequences), within, or downstream (3' non-coding sequences) of a coding sequence, and which influence the transcription, RNA processing or stability, or translation of the associated coding sequence. Regulatory sequences include, but are not limited to, enhancers, introns, translation leader sequences, non-translated leader sequences, and polyadenylation signal sequences.

The expression cassette also can optionally include a transcriptional and/or translational termination region (i.e., termination region) that is functional in the cell. A variety of transcriptional terminators are available for use in expression cassettes and are responsible for the termination of transcription beyond the transgene and correct mRNA polyadenylation. The termination region may be native to the transcriptional initiation region, may be native to the operably linked nucleotide sequence of interest, may be native to the host, or may be derived from another source (i.e., foreign or heterologous to the promoter, the nucleotide sequence of interest, the host, or any combination thereof). In addition, a coding sequence's native transcription terminator can be used.

A signal sequence can be operably linked to nucleic acids of the present invention to direct the nucleotide sequence into a cellular compartment. In this manner, the expression cassette will comprise a nucleotide sequence encoding the interfering RNA operably linked to a nucleic acid sequence for the signal sequence. The signal sequence may be operably linked at the N- or C-terminus of the interfering RNA.

Regardless of the type of regulatory sequence(s) used, they can be operably linked to the nucleotide sequence of the antisense RNA or interfering RNA. As used herein, "operably linked" means that elements of a nucleic acid construct such as an expression cassette are configured so as to perform their usual function. Thus, regulatory or control sequences (e.g., promoters) operably linked to a nucleotide sequence of interest are capable of effecting expression of the nucleotide sequence of interest. The control sequences need not be contiguous with the nucleotide sequence of interest, so long as they function to direct the expression thereof. Thus, for example, intervening untranslated, yet transcribed, sequences can be present between a promoter and a coding sequence, and the promoter sequence can still be considered "operably linked" to the coding sequence. A nucleotide sequence of the present invention (i.e., an antisense RNA or interfering RNA) can be operably linked to a regulatory sequence, thereby allowing its expression in a cell and/or subject.

The expression cassette also can include a nucleotide sequence for a selectable marker, which can be used to select a transformed cell or subject. As used herein, "selectable marker" means a nucleic acid that when expressed imparts a distinct phenotype to the cell or subject expressing the marker and thus allows such transformed cells or subjects to be distinguished from those that do not have the marker. Such a nucleic acid may encode either a selectable or screenable marker, depending on whether the marker confers a trait that can be selected for by chemical means, such as by using a selective agent (e.g., an antibiotic or the like), or on whether the marker is simply a trait that one can identify through observation or testing, such as by screening. Of course, many examples of suitable selectable markers are known in the art and can be used in the expression cassettes described herein.

Examples of selectable markers include, but are not limited to, a nucleic acid encoding neo or nptII, which confers resistance to kanamycin, G418, and the like (Potrykus et al., Mol. Gen. Genet. 199:183 (1985)); a nucleic acid encoding a nitrilase such as bxn from *Klebsiella ozaenae* that confers resistance to bromoxynil (Stalker et al., *Science* 242:419 (1988)); a nucleic acid encoding an altered acetolactate synthase (ALS) that confers resistance to imidazolinone, sulfonylurea or other ALS-inhibiting chemicals (EP Patent Application No. 154204); a nucleic acid encoding a methotrexate-resistant dihydrofolate reductase (DHFR) (Thillet et al., *J. Biol. Chem.* 263:12500 (1988)); a nucleic acid encoding a dalapon dehalogenase that confers resistance to dalapon; a nucleic acid encoding a mannose-6-phosphate isomerase (also referred to as phosphomannose isomerase (PMI)) that confers an ability to metabolize mannose (U.S. Pat. Nos. 5,767,378 and 5,994,629); a nucleic acid encoding an altered anthranilate synthase that confers resistance to 5-methyl tryptophan; and/or a nucleic acid encoding hph that confers resistance to hygromycin. One of skill in the art is capable of choosing a suitable selectable marker for use in an expression cassette.

Additional selectable markers include, but are not limited to, a nucleic acid encoding β-glucuronidase or uidA (GUS) that encodes an enzyme for which various chromogenic substrates are known; a nucleic acid encoding β-lactamase, an enzyme for which various chromogenic substrates are known (e.g., PADAC, a chromogenic cephalosporin) (Sutcliffe, *Proc. Natl. Acad. Sci. USA* 75:3737 (1978)); a nucleic acid encoding xylE that encodes a catechol dioxygenase (Zukowsky et al., *Proc. Natl. Acad. Sci. USA* 80:1101 (1983)); a nucleic acid encoding tyrosinase, an enzyme capable of oxidizing tyrosine to DOPA and dopaquinone, which in turn condenses to form melanin (Katz et al., *J. Gen. Microbiol.* 129:2703 (1983)); a nucleic acid encoding β-galactosidase, an enzyme for which there are chromogenic substrates; a nucleic acid encoding luciferase (lux) that allows for bioluminescence detection (Ow et al., *Science* 234:856 (1986)); a nucleic acid encoding acquorin which may be employed in calcium-sensitive bioluminescence detection (Prasher et al., (1985) *Biochem. Biophys. Res. Comm.* 126:1259 (1985)); or a nucleic acid encoding green fluorescent protein (Niedz et al., *Plant Cell Reports* 14:403 (1995)). One of skill in the art is capable of choosing a suitable selectable marker for use in an expression cassette.

In some embodiments of the present invention, the expression cassette can comprise an expression control sequence operatively linked to a nucleotide sequence that is a template for one or both strands of the interfering RNA. The interfering RNA template comprises (a) a first (antisense) stand having a sequence complementary to from about 15 to about 30 consecutive nucleotides of the nucleotide sequence of PTBP1; and (b) a second (sense) strand having a nucleotide sequence fully complementary or substantially complementary to the first strand. In further embodiments, a promoter can flank either end of the template nucleotide sequence, wherein the promoters drive expression of each individual DNA strand, thereby generating two complementary (or substantially complementary) RNAs that hybridize and form the interfering RNA. In alternative embodiments, the nucleotide sequence is transcribed into both strands of the interfering RNA on one transcription unit, wherein the sense strand is transcribed from the 5' end of the transcription unit and the antisense strand is transcribed from the 3' end, wherein the two strands are separated by about 3 to about 500 basepairs, and wherein after transcription, the RNA transcript folds on itself to form a shRNA molecule.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "substantially identical" or "corresponding to" means that two nucleic acid sequences have at least about 80% sequence identity. In some embodiments, the two nucleic acid sequences can have at least about 85%, 90%, 95%, 96%, 97%, 98%, 99% or 100% sequence identity.

An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). In some embodiments, "percent identity" can refer to the percentage of identical amino acids in an amino acid sequence.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Adv. Appl. Math.* 2:482 (1981); Smith et al., *Nucleic Acids Res.* 11:2205 (1983)).

Useful methods for determining sequence identity are also disclosed in Guide to Huge Computers (Martin J. Bishop, ed., Academic Press, San Diego (1994)), and Carillo, H., and Lipton, D., *Applied Math* 48: 1073 (1988)). More particularly, preferred computer programs for determining sequence identity include but are not limited to the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; (Altschul et al., *J. Mol. Biol.* 215:403 (1990)); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity.

One aspect of the invention relates to an expression cassette comprising a polynucleotide encoding an antisense RNA or an interfering RNA targeted to a polynucleotide encoding a mammalian polypyrimidine tract binding protein 1 (PTBP1). In some embodiments, the PTBP1 is a human PTBP1.

The amino acid sequence of PTBP1 and the nucleotide sequence encoding PTBP1 are well known in the art and available in sequences databases such as GenBank. An exemplary cDNA sequence of human PTBP1 is Accession No. BC002397 (SEQ ID NO:12).

The expression cassette may be any type of expression cassette suitable for delivering the polynucleotide to a cell or subject. The expression cassette may be part of a delivery vector. The vector can be delivered to cells in vitro or in vivo. In other embodiments, the vector can be delivered to cells ex vivo, and then cells containing the vector are delivered to the subject. The choice of delivery vector can be made based on a number of factors known in the art, including age and species of the target host, in vitro versus in vivo delivery, level and persistence of expression desired, intended purpose (e.g., for therapy or screening), the target cell or organ, route of delivery, size of the isolated polynucleotide, safety concerns, and the like.

Suitable vectors include plasmid vectors, viral vectors (e.g., retrovirus, alphavirus; vaccinia virus; adenovirus, adeno-associated virus and other parvoviruses, lentivirus, poxvirus, or herpes simplex virus), lipid vectors, poly-lysine vectors, synthetic polyamino polymer vectors, and the like. In one embodiment, the expression cassette is in an AAV vector.

In some embodiments, the polynucleotide encodes an antisense RNA targeted to a mammalian PTBP1. In other embodiments, the polynucleotide encodes an interfering RNA targeted to a mammalian PTBP1 protein, e.g., a shRNA, a siRNA, or a miRNA.

In a particular embodiment, the interfering RNA is a siRNA comprising the nucleotide sequence of SEQ ID NO: 1 or SEQ ID NO: 2 or a nucleotide sequence at least 90% identical thereto, e.g., at least 90%, 91%, 92%, 93%, 94%, 95%, 96%, 97%, 98%, or 99% identical.

In some embodiments, the polynucleotide is operably linked to a promoter. In one embodiment, the promoter is a constitutive promoter. A constitutive promoter is advantageous in the present invention as it ensures that the antisense RNA or interfering RNA continues to be expressed as the oligodendrocyte or oligodendrocyte precursor cell transdifferentiates to a neuron. Alternatively, a cell-type specific promoter may be used, e.g., an oligodendrocyte-specific promoter.

Another aspect of the invention relates to a virus particle comprising the expression cassette of the invention. The virus particle packages (i.e., encapsidates) a vector genome, optionally an AAV vector genome. In particular embodiments, the invention provides an AAV particle comprising an AAV capsid, wherein the AAV capsid packages an AAV vector genome.

In some embodiments, the virus particle has a tropism for oligodendrocytes and/or oligodendrocyte precursor cells. Examples of virus particles with this tropism are known in the art. In some embodiments, the virus particle with a tropism for oligodendrocytes and/or oligodendrocyte precursor cells is an AAV particle, e.g., an AAV particle having a modified capsid protein that provides the tropism, e.g., is one described in U.S. Publication No. 2015/0238550 or International Publication No. WO 2016/081811, incorporated by reference herein in their entirety.

A further aspect of the invention relates to a composition comprising the expression cassette and/or the virus particle of the invention. In some embodiments, the composition is a pharmaceutical composition comprising the expression cassette and/or the virus particle of the invention and a pharmaceutically acceptable carrier.

The present invention further provides methods of producing the virus vectors of the invention. In a representative embodiment, the present invention provides a method of producing a recombinant virus vector, the method comprising providing to a cell in vitro, (a) a template comprising (i) a heterologous nucleic acid, and (ii) packaging signal sequences sufficient for the encapsidation of the AAV template into virus particles (e.g., one or more (e.g., two) terminal repeats, such as AAV terminal repeats), and (b) AAV sequences sufficient for replication and encapsidation of the template into virus particles (e.g., the AAV rep and AAV cap sequences). The template and AAV replication and capsid sequences are provided under conditions such that recombinant virus particles comprising the template packaged within the capsid are produced in the cell. The method can further comprise the step of collecting the virus particles from the cell. Virus particles may be collected from the medium and/or by lysing the cells.

In one illustrative embodiment, the invention provides a method of producing a rAAV particle comprising an AAV capsid, the method comprising: providing a cell in vitro with a nucleic acid encoding AAV rep and cap coding sequences, an AAV vector genome comprising a heterologous nucleic acid, and helper functions for generating a productive AAV infection; and allowing assembly of the AAV particles comprising the AAV capsid and encapsidating the AAV vector genome.

The cell is typically a cell that is permissive for AAV viral replication. Any suitable cell known in the art may be employed, such as mammalian cells. Also suitable are trans-complementing packaging cell lines that provide functions deleted from a replication-defective helper virus, e.g., 293 cells or other Ela trans-complementing cells.

The AAV replication and capsid sequences may be provided by any method known in the art. Current protocols typically express the AAV replcap genes on a single plasmid. The AAV replication and packaging sequences need not be provided together, although it may be convenient to do so. The AAV rep and/or cap sequences may be provided by any viral or non-viral vector. For example, the replcap sequences may be provided by a hybrid adenovirus or herpesvirus vector (e.g., inserted into the Ela or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an EBV based nuclear episome.

As a further alternative, the rep/cap sequences may be stably carried (episomal or integrated) within a cell.

Typically, the AAV rep/cap sequences will not be flanked by the AAV packaging sequences (e.g., AAV ITRs), to prevent rescue and/or packaging of these sequences.

The template (e.g., an rAAV vector genome) can be provided to the cell using any method known in the art. For example, the template may be supplied by a non-viral (e.g., plasmid) or viral vector. In particular embodiments, the template is supplied by a herpesvirus or adenovirus vector (e.g., inserted into the Ela or E3 regions of a deleted adenovirus). As another illustration, Palombo et al., (1998) *J. Virol.* 72:5025, describe a baculovirus vector carrying a reporter gene flanked by the AAV ITRs. EBV vectors may also be employed to deliver the template, as described above with respect to the replcap genes.

In another representative embodiment, the template is provided by a replicating rAAV virus. In still other embodiments, an AAV provirus is stably integrated into the chromosome of the cell.

To obtain maximal virus titers, helper virus functions (e.g., adenovirus or herpesvirus) essential for a productive AAV infection are generally provided to the cell. Helper virus sequences necessary for AAV replication are known in the art. Typically, these sequences are provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes required for efficient AAV production as described by Ferrari et al., (1997) *Nature Med.* 3:1295, and U.S. Pat. Nos. 6,040,183 and 6,093,570.

Further, the helper virus functions may be provided by a packaging cell with the helper genes integrated in the chromosome or maintained as a stable extrachromosomal element. In representative embodiments, the helper virus sequences cannot be packaged into AAV virions, e.g., are not flanked by AAV ITRs.

Those skilled in the art will appreciate that it may be advantageous to provide the AAV replication and capsid sequences and the helper virus sequences (e.g., adenovirus sequences) on a single helper construct. This helper construct may be a non-viral or viral construct, but is optionally a hybrid adenovirus or hybrid herpesvirus comprising the AAV rep/cap genes.

In one particular embodiment, the AAV replcap sequences and the adenovirus helper sequences are supplied by a single adenovirus helper vector. This vector further contains the rAAV template. The AAV rep/cap sequences and/or the rAAV template may be inserted into a deleted region (e.g., the Ela or E3 regions) of the adenovirus.

In a further embodiment, the AAV rep/cap sequences and the adenovirus helper sequences are supplied by a single adenovirus helper vector. The rAAV template is provided as a plasmid template.

In another illustrative embodiment, the AAV rep/cap sequences and adenovirus helper sequences are provided by a single adenovirus helper vector, and the rAAV template is integrated into the cell as a provirus. Alternatively, the rAAV template is provided by an EBV vector that is maintained within the cell as an extrachromosomal element (e.g., as a "EBV based nuclear episome," see Margolski, (1992) *Curr. Top. Microbiol. Immun.* 158:67).

In a further exemplary embodiment, the AAV rep/cap sequences and adenovirus helper sequences are provided by a single adenovirus helper. The rAAV template is provided as a separate replicating viral vector. For example, the rAAV template may be provided by a rAAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the rAAV template are embedded in the adenovirus backbone and are flanked by the 5' and 3' cis sequences, so that these sequences may be packaged into adenovirus capsids. As described above, in representative embodiments, the adenovirus helper sequences and the AAV rep/cap sequences are not flanked by the AAV packaging sequences (e.g., the AAV ITRs), so that these sequences are not packaged into the AAV virions.

Herpesvirus may also be used as a helper virus in AAV packaging methods. Hybrid herpesviruses encoding the AAV rep protein(s) may advantageously facilitate for more scalable AAV vector production schemes. A hybrid herpes simplex virus type I (HSV-1) vector expressing the AAV-2 rep and cap genes has been described (Conway et al., (1999) *Gene Therapy* 6:986 and WO 00/17377, the disclosures of which are incorporated herein in their entireties).

As a further alternative, the virus vectors of the invention can be produced in insect cells using baculovirus vectors to deliver the rep/cap genes and rAAV template as described by Urabe et al., (2002) *Human Gene Therapy* 13:1935-43.

Other methods of producing AAV use stably transformed packaging cells (see, e.g., U.S. Pat. No. 5,658,785).

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al., (1999) *Gene Therapy* 6:973). In representative embodiments, deleted replication-defective helper viruses are used so that any contaminating helper virus is not replication competent. As a further alternative, an adenovirus helper lacking late gene expression may be employed, as only adenovirus early gene expression is required to mediate packaging of AAV virus. Adenovirus mutants defective for late gene expression are known in the art (e.g., ts100K and ts149 adenovirus mutants).

The inventive packaging methods may be employed to produce high titer stocks of virus particles. In particular embodiments, the virus stock has a titer of at least about $10^5$ transducing units (tu)/ml, at least about $10^6$ tu/ml, at least about $10^7$ tu/ml, at least about $10^8$ tu/ml, at least about $10^9$ tu/ml, or at least about $10^{10}$ tu/ml.

A further aspect of the invention relates to a method of attenuating expression of PTBP1 in a cell, comprising contacting the cell with the expression cassette, virus particle, and/or composition of the invention, wherein the expression of PTBP1 is attenuated. In some embodiments, the cell is an oligodendrocyte or oligodendrocyte precursor cell. In certain embodiments, the expression of PTBP1 is attenuated by at least about 50%, e.g., at least about 60%, 70%, 80%, 90%, or 95%.

Another aspect of the invention relates to a method of transdifferentiating an oligodendrocyte or an oligodendrocyte precursor cell to a neuron, comprising contacting the oligodendrocyte or oligodendrocyte precursor cell with the expression cassette, virus particle, and/or composition of the invention, thereby transdifferentiating the oligodendrocyte or oligodendrocyte precursor cell to a neuron.

The transdifferentiation process may be monitored and/or confirmed by observing the morphological, immunohistochemical, and/or functional properties of the cell by methods known in the art and as described herein. For example, the transdifferentiation process may be monitored and/or confirmed by measuring the disappearance of oligodendrocyte markers (e.g., olig2) and the appearance of neuron markers (e.g., NeuN) in the cell. The process may also be monitored and/or confirmed by detecting the appearance of electrical activity (e.g., action potentials) in the cell.

In each of these methods, the cell may be an in vitro cell, e.g., a cultured cell or a cell line. In certain embodiments, the cell is an ex vivo cell, e.g., a primary cell isolated from a subject. In other embodiments, the cell is an in vivo cell, e.g., a cell in a mammalian subject. The subject may be a laboratory animal used for research purposes. In some embodiments, the subject is a patient, e.g., one in need of therapy.

An additional aspect of the invention relates to a method of increasing the number of neurons in the brain of a mammalian subject, comprising delivering to the brain the expression cassette, virus particle, and/or composition of the invention, thereby increasing the number of neurons in the brain of the mammalian subject relative to the number of neurons prior to the delivery.

A further aspect of the invention relates to a method of transdifferentiating an oligodendrocyte or an oligodendrocyte precursor cell to a neuron in the brain of a mammalian subject, comprising delivering to the brain the expression cassette, virus particle, and/or composition of the invention, thereby transdifferentiating an oligodendrocyte or an oligodendrocyte precursor cell to a neuron in the brain of the mammalian subject.

In some embodiments, the mammalian subject is a laboratory animal. In some embodiments, the mammalian subject is a human subject.

The expression cassette, virus particle, and/or composition of the invention may be delivered to the brain by any suitable technique. In some embodiments, the expression cassette, virus particle, and/or composition is injected directly into the brain, e.g., into a region of the brain such as the striatum. In other embodiments, the expression cassette, virus particle, and/or composition is injected in a manner that provides access to the brain, e.g., intracerebroventricular or intrathecal injection.

Another aspect of the invention relates to a method of treating a central nervous system disorder or condition responsive to an increase in the number of neurons in a mammalian subject in need thereof, the method comprising delivering to the brain the expression cassette, virus particle, and/or composition of the invention, thereby treating the central nervous system disorder or condition. The subject may be any subject in need of treatment. In some embodiments, the mammalian subject is a laboratory animal. In some embodiments, the mammalian subject is a human subject.

The disorder or condition may be any one in which an increase in the number of neurons in the brain would be beneficial, e.g., would improve at least one symptom of the disorder or condition. In some embodiments, the disorder or condition is a neurodegenerative disorder, e.g., Parkinson's disease, Alzheimer's disease, Huntington's chorea, or amyotrophic lateral sclerosis. In some embodiments, the disorder or condition is a traumatic brain or spinal cord injury or stroke. In some embodiments, the disorder or condition is a natural condition such as aging.

In certain embodiments, the methods of the invention may further comprise administering an additional compound, molecule, or agent to enhance transdifferentiation of the cell. In some embodiments, the methods further comprise delivering to the oligodendrocyte or oligodendrocyte precursor cell or the brain a differentiation factor that promotes transdifferentiation to neurons. The differentiation factor may be, without limitation, NeuroD1, Ascl1, Brn2a, Mytl1, SOX2, or any combination thereof.

In other embodiments, the methods further comprise delivering to the oligodendrocyte or oligodendrocyte precursor cell or the brain an inhibitor of expression and/or activity of a factor, the inhibition of which results in transdifferentiation to neurons. In one embodiment, the methods further comprise delivering to the oligodendrocyte or oligodendrocyte precursor cell or the brain an inhibitor of expression of the REI silencing transcription factor complex. The inhibitor may be, for example, an antisense RNA or an interfering RNA targeted to one or more polynucleotides encoding proteins in the complex.

In some embodiments, the methods further comprise delivering to the oligodendrocyte or oligodendrocyte precursor cell or the brain a factor that promote neuron growth, e.g., a growth factor or neurotrophic factor such as nerve growth factor, brain-derived neurotrophic factor, glial cell line-derived neurotrophic factor, neurotrophin-3, neurotrophin-4, and ciliary neurotrophic factor.

In some embodiments, the methods further comprise delivering to the oligodendrocyte or oligodendrocyte precursor cell or the brain an additional therapeutic agent for the disorder or condition be treated. Any suitable therapeutic agent known in the art to be useful for treating the particular disorder or condition may be used. Examples of therapeutic agents for neurological disorders include, without limitation, for Alzheimer's disease: caprylidene, donepezil, galantamine, tacrine, vitamin E, ergoloid mesylates, rivastigmine; for Parkinson's disease: nadolol, zonisamide, amantadine, apomorphine, belladonna, benztropine, biperiden, bromocriptine, carbidopa, entacapone, levodopa, pergolide mesylate, pramipexole, procyclidine, rasagiline, ropinirole, rotiotine, scopolamine, tolcapone, trihexylphenidyl, rivastigmine, seleginline; for Huntington's disease: baclofen, pregabalin, tetrabenazine, methylprednisolone, desvenlafaxine, nortriptyline; and for dementia: haloperidol and ergoloid mesylates; for amyotrophic lateral sclerosis: riluzole, edaravone; for traumatic brain or spinal cord injury: diuretics (e.g., mannitol, furosemide, glycerol, urea), anti-seizure drugs, coma-inducing drugs; for stroke: anticoagulants/antiplatelets (e.g., aspirin, warfarin), antihypertensives, tissue plasminogen activator.

In these embodiments, the additional compound, molecule, or agent may be delivered by contacting the oligodendrocyte or oligodendrocyte precursor cell or the brain with the additional compound, molecule, or agent itself or with an expression vector encoding the additional compound, molecule, or agent.

Recombinant virus vectors according to the present invention find use in both veterinary and medical applications. Suitable subjects include both avians and mammals. The term "avian" as used herein includes, but is not limited to, chickens, ducks, geese, quail, turkeys, pheasant, parrots, parakeets. The term "mammal" as used herein includes, but is not limited to, humans, non-human primates (e.g., monkeys and baboons), cattle, sheep, goats, pigs, horses, cats, dogs, rabbits, rodents (e.g., rats, mice, hamsters, and the like), etc. Human subjects include neonates, infants, juveniles, and adults. Optionally, the subject is "in need of" the methods of the present invention, e.g., because the subject has or is believed at risk for a disorder including those described herein or that would benefit from the delivery of a nucleic acid including those described herein. For example, in particular embodiments, the subject has (or has had) or is at risk for a neurodegenerative disorder or a spinal cord or brain injury. As a further option, the subject can be a laboratory animal and/or an animal model of disease.

In particular embodiments, the present invention provides a pharmaceutical composition comprising an expression vector, virus particle and/or composition of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and will preferably be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a nucleotide sequence to a cell in vitro. The virus vector may be introduced to the cells at the appropriate multiplicity of infection according to standard transduction methods appropriate for the particular target cells. Titers of the virus vector or capsid to administer can vary, depending upon the target cell type and number, and the particular virus vector or capsid, and can be determined by those of skill in the art without undue experimentation. In particular embodiments, at least about $10^3$ infectious units, more preferably at least about $10^5$ infectious units are introduced to the cell.

The virus vectors may be introduced to cells in vitro for the purpose of administering the modified cell to a subject. In particular embodiments, the cells have been removed from a subject, the virus vector is introduced therein, and the cells are then replaced back into the subject. Methods of removing cells from a subject for treatment ex vivo, followed by introduction back into the subject are known in the art (see, e.g., U.S. Pat. No. 5,399,346). Alternatively, the recombinant virus vector is introduced into cells from another subject, into cultured cells, or into cells from any other suitable source, and the cells are administered to a subject in need thereof.

Dosages of the cells to administer to a subject will vary upon the age, condition and species of the subject, the type of cell, the nucleic acid being expressed by the cell, the mode of administration, and the like. Typically, at least about $10^2$ to about $10^8$ or about $10^3$ to about $10^6$ cells will be administered per dose in a pharmaceutically acceptable carrier. In particular embodiments, the cells transduced with the virus vector are administered to the subject in an effective amount in combination with a pharmaceutical carrier.

A further aspect of the invention is a method of administering the virus vectors of the invention to subjects. In particular embodiments, the method comprises a method of delivering a nucleic acid of interest to an animal subject, the method comprising: administering an effective amount of a virus vector according to the invention to an animal subject. Administration of the virus vectors of the present invention to a human subject or an animal in need thereof can be by any means known in the art. Optionally, the virus vector is delivered in an effective dose in a pharmaceutically acceptable carrier.

Dosages of the virus vectors to be administered to a subject will depend upon the mode of administration, the disease or condition to be treated, the individual subject's condition, the particular virus vector, and the nucleic acid to be delivered, and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$ transducing units or more, e.g., about $10^7$, $10^8$, $10^9$, $10^{10}$, $10^{11}$, $10^{12}$, $10^{13}$ $10^{14}$, $10^{15}$, or $10^{16}$, transducing units, e.g., about $10^{12}$ to $10^{14}$ transducing units.

In particular embodiments, more than one administration (e.g., two, three, four or more administrations) may be employed to achieve the desired level of gene expression over a period of various intervals, e.g., daily, weekly, monthly, yearly, etc.

In some embodiments, the viral vector is administered directly to the CNS, e.g., the brain or the spinal cord. Direct administration can result in high specificity of transduction of oligodendrocytes, e.g., wherein at least 80%, 85%, 90%, 95% or more of the transduced cells are oligodendrocytes. Any method known in the art to administer vectors directly to the CNS can be used. The vector may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes, cortex, basal ganglia, hippocampus and amygdala), limbic system, neocortex, corpus striatum, cerebrum, and inferior colliculus. The vector may also be administered to different regions of the eye such as the retina, cornea or optic nerve. The vector may be delivered into the cerebrospinal fluid (e.g., by lumbar puncture) for more disperse administration of the vector.

The delivery vector may be administered to the desired region(s) of the CNS by any route known in the art, including but not limited to, intrathecal, intracerebral, intraventricular, intranasal, intra-aural, intra-ocular (e.g., intravitreous, sub-retinal, anterior chamber) and peri-ocular (e.g., sub-Tenon's region) delivery or any combination thereof.

Typically, the viral vector will be administered in a liquid formulation by direct injection (e.g., stereotactic injection) to the desired region or compartment in the CNS. In some embodiments, the vector can be delivered via a reservoir and/or pump. In other embodiments, the vector may be provided by topical application to the desired region or by intra-nasal administration of an aerosol formulation. Administration to the eye or into the car, may be by topical application of liquid droplets. As a further alternative, the vector may be administered as a solid, slow-release formulation. Controlled release of parvovirus and AAV vectors is described by international patent publication WO 01/91803.

In some embodiments where the subject has a compromised blood-brain barrier (BBB), the viral vector can be delivered systemically (e.g., intravenously) to the subject, wherein the vector transduces oligodendrocytes in the area of (e.g., bordering) the BBB compromise. In certain embodiments, the vector transduces cells in the compromised area but not cells in uncompromised areas. Thus, one aspect of the invention relates to a method of delivering a nucleic acid of interest to an area of the CNS bordering a compromised blood brain barrier area in a mammalian subject, the method comprising intravenously administering an effective amount of the AAV particle of the invention.

In some embodiments, the compromise in the BBB is due to a disease or disorder. Examples include, without limitation, neurodegenerative diseases such as Alzheimer's disease, Parkinson's disease, amyotrophic lateral sclerosis, multiple sclerosis, epilepsy, CNS tumors, and/or cerebral infarct. In other embodiments, the BBB compromise can be an induced disruption, e.g., to promote delivery of agents to the CNS. Temporary BBB compromise can be induced by, for example, toxic chemicals (such as metrazol, VP-16, cisplatin, hydroxyurea, fluorouracil, and etoposide), osmotic agents (such as mannitol and arabinose), biological agents (such as retinoic acid, phorbol myristate acetate, leukotriene C4, bradykinin, histamine, RMP-7, and alkylglycerols), or irradiation (such as ultrasound or electromagnetic radiation).

Delivery to any of these tissues can also be achieved by delivering a depot comprising the virus vector, which can be implanted into the tissue or the tissue can be contacted with a film or other matrix comprising the virus vector. Examples of such implantable matrices or substrates are described in U.S. Pat. No. 7,201,898.

Injectables can be prepared in conventional forms, either as liquid solutions or suspensions, solid forms suitable for solution or suspension in liquid prior to injection, or as emulsions. Alternatively, one may administer the virus vector in a local rather than systemic manner, for example, in a depot or sustained-release formulation. Further, the virus vector can be delivered dried to a surgically implantable matrix such as a bone graft substitute, a suture, a stent, and the like (e.g., as described in U.S. Pat. No. 7,201,898).

Pharmaceutical compositions suitable for parenteral administration can comprise sterile aqueous and non-aqueous injection solutions of the composition of this invention, which preparations are optionally isotonic with the blood of the intended recipient. These preparations can contain antioxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions can be presented in unit/dose or multi-dose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 1 µg to about 10 grams of the composition of this invention. When the composition is substantially water-insoluble, a sufficient amount of emulsifying agent, which is physiologically acceptable, can be included in sufficient quantity to emulsify the composition in an aqueous carrier. One such useful emulsifying agent is phosphatidyl choline.

Having described the present invention, the same will be explained in greater detail in the following examples, which are included herein for illustration purposes only, and which are not intended to be limiting to the invention.

Example 1

Methods siRNA and expression plasmid co-transfection: Four unique ptbp1 siRNAs and a non-targeting control siRNA were tested (Thermo Scientific ON-TARGETplus Rat ptbp1 gene, Thermo Scientific, Waltham, MA). The ptbp1 siRNA sequences were:

1) CGGCAUCGUCCCAGACAUA (SEQ ID NO: 1),
2) CAAUGGCGGUGUGGUCAAA (SEQ ID NO: 2),
3) CAACUUGAACCCUGAGAGA (SEQ ID NO: 3), and
4) CCAACACUAUGGUUAACUA (SEQ ID NO: 4).
    siRNA was co-transfected with a CMV-promoter containing, DDK-tagged rat ptbp1 expression plasmid (Origene) into HeLa cells in accordance with published Lipofectamine 2000 plasmid/siRNA co-transfection protocols (Life Technologies, Carlsbad, CA). siRNA was resuspended in siRNA buffer (Thermo Scientific, Waltham, MA). Transfection was performed into 80% confluent 12-well plates, with a volume of 1 mL antibiotic-frecc media. A total of 200 ng plasmid DNA and 20 pmol dsRNA was mixed with 100 µL optimum and 4 µL Lipofectamine 2000, and added to each well.

miRNA plasmid production: The BLOCK-iT™ Pol II miR RNAi expression vector kit (Invitrogen, La Jolla, CA) was used to prepare pol II-based miRNA from the successful siRNA constructs. In accordance with kit instructions miRNA primers were designed based on the two most successful siRNA sequences (siRNA 3 (SEQ ID NO: 3) and 4 (SEQ ID NO: 4)). Sequences designed to match PTBP1 siRNA 3 and 4 were as follows: siRNA 3) Top:

TGCTGTCTCT CAGGGTTCAA GTTGCTGTTT TGGC-CACTGA CTGACAGCAA CTTACCCTGA GAGA (SEQ ID NO: 5), Bottom: CCTGTCTCTC AGGGTAAGTT GCTGTCAGTC AGTGGCCAAA ACAGCAACTT GAACCCTGAG AGAC (SEQ ID NO: 6); siRNA 4) Top: TGCTGTAGTT AACCATAGTG TTGGCAGTTT TGGC-CACTGA CTGACTGCCA ACAATGGTTA ACTA (SEQ ID NO: 7), Bottom: CCTGTAGTTA ACCATTGTTG GCAGTCAGTC AGTGGCCAAA ACTGCCAACA CTATGGTTAA CTAC (SEQ ID NO: 8). Primers were prepared by Integrated DNA technologies (Coralville, IA). Primers were annealed and ligated with pre-cut pcDNA 6.2-EmGFP plasmid per manufacturer's instructions. Using high fidelity PCR (Phusion, New England Biotechnologies, Ipswich, MA), sequences were amplified for the non-specific miRNA (included with the BLOCK-iT kit), and PTBP1 miRNAs 3 and 4, along with their 5' and 3' miR flanking regions from the pcDNA 6.2-EmGFP plasmid using primers containing a short overhang and a Not-1 restriction sequence: forward: AGCTGCGGCC GCAGGGAGGT AGTGAGTCGAC (SEQ ID NO: 9), reverse: TCATGCGGCC GCGAAAGCTG GGTCTAGATA TC (SEQ ID NO: 10). Amplified products were gel purified, digested with Not-1 restriction enzyme (NEB), and ligated immediately after the stop codon of EGFP in the plasmid TR-CBA-EGFP. Plasmid sequences were verified using a primer within the EGFP sequence: CGACAACCAC TACCTGAGC (SEQ ID NO: 11).

Virus production: Virus was produced in HEK-293 cells as previously described (Greiger et al., Nat. Protoc. 1:1412 (2006)). Briefly, polyethylenimine max (PEI) was used for the triple transfection of the pXR2 or pOLIGO001 cap and rep plasmid, the pXX6-80 helper plasmid, and the TR-EGFP plasmid containing the nonspecific miRNA, or ptbp1 miRNA-3 or miRNA-4 flanked by inverted terminal repeats under the chicken beta actin (CBA) promoter. Cells were harvested between 48 and 72 h post-transfection, and virus was purified by cesium chloride ultracentrifugation. After identifying peak fractions by quantitative PCR (qPCR), virus was dialyzed into phosphate-buffered saline (PBS). Titers were calculated by qPCR according to established procedures using a LightCycler 480 instrument and SV40 pA primers (Greiger et al., Nat. Protoc. 1:1412 (2006)).

Transduction/transfection verification of miRNA: rAAV2-packaged EGFP-miRNA virus was delivered at $1 \times 10^5$ moi to HEK293 cells immediately upon splitting onto 12 well plates ($2 \times 10^5$ cells per well). 24 h post-transduction 100 ng of rat ptbp1 expression plasmid was transfected into cells using PEI (0.8 µL in 5 µL serum-free RPMI).

Electrophoresis and Western blot: For both siRNA and AAV2/miRNA knockdown studies, 48 h post-transfection cells were harvested by washing in ice-cold PBS and lysed in a buffer containing 150 mM NaCl, 50 mM Tris-HCl (pH 8), 0.1% NP40, 50 mM NaF, 30 mM β-glycerophosphate, 1 mM $Na_3 VO_4$ and 1× Complete Protease Inhibitor cocktail (Roche). Equal amounts of proteins were electrophoresed on a 10% SDS-PAGE denaturing gel, followed by transfer onto a Hybond™-ECL nitrocellulose membrane (GE Healthcare). The membrane was blocked with 5% fat-free powdered milk for 1 hour at room temperature, followed by overnight incubation at 4° C. in anti-DDK (Origene) in 5% BSA. Tubulin (Cell Signaling) was used as a loading control. After washing, the membranes were incubated with anti-rabbit IgG-HRP. Bands were visualized by chemiluminescence.

Animals and Stereotactic Infusions: All of the animals were male Sprague-Dawley rats (Charles River, Morrisville, NC, USA) weighing approximately 300 g at time of intracranial injection. The animals were maintained on a 12-h light-dark cycle and had free access to water and food. For all animal studies, care and procedures were in accordance with the National Institutes of Health Guide for the Care and Use of Laboratory Animals, and all procedures received prior approval by the University of North Carolina Institutional Animal Care and Usage Committee.

Virus vector infusions were performed as previously described (Haberman et al., *Nat. Med.* 9:1076 (2003)). First, animals were anesthetized with 50 mg/kg pentobarbital and placed into a stereotactic frame. Using a 32 gauge stainless steel injector and a Sage infusion pump, animals received 2 μl unilaterally of either OLIG001 AAV-GFP or OLIG001 AAV-4miRNA-GFP over 10 minutes into the striatum (0.5 mm anterior to Bregma, 3.5 mm lateral, 5.5 mm vertical, according to the atlas of Paxinos and Watson (Paxinos et al., *The Rat Brain in Stereotaxic Coordinates.* 4th ed., Academic Press, New York, USA, 1998). The injector was left in place for 3 minutes post-infusion in order to allow diffusion from the injector. For the fluorescent bead injections, 3 months after the striatal 4miRNA virus infusion, rats were anesthetized and placed into the stereotactic frame. Subsequently fluorescent latex beads (0.5 μl/5 minutes, Fluospheres 580/605, 1:5 dilution, Molecular Probes Millipore) were infused into the globus pallidus (1.0 mm posterior to Bregma, 3.0 mm lateral, 7.0 mm vertical) or the substantia nigra (5.3 mm posterior to Bregma, 2.5 mm lateral, 8.0 mm vertical). The injector was left in place for 3 minutes post-infusion in order to allow diffusion from the injector.

Immunohistochemistry and confocal microscopy: Ten days, 3 months or 6 months after the vector infusion animals received an overdose of pentobarbital (100 mg/kg pentobarbital, ip) and were perfused transcardially with ice-cold 100 mM sodium phosphate-buffered saline (PBS) (pH 7.4), followed by 4% paraformaldehyde in PB (pH 7.4). After brains were post-fixed 12-48 h at 4° C. in the paraformaldehyde-PB, 40 μm coronal sections were cut using a vibrating blade microtome for subsequent immunofluorescence. The sections were washed 3× in PBS and blocked in 10% goat serum/PBS for 45 minutes. In order to determine GFP cellular co-localization, tissue sections were incubated in the blocking solution with one of the following antibody cellular markers: NeuN (1:500, Chemicon); GFAP (1:2000, Dako); Olig2 (1:500, Millipore); DARPP32 (1:500, ABCAM); parvalbumin (1:500, Millipore). Following incubation at 4° C. for 48-72 h in primary antibodies, the sections were rinsed 3× with PBS and blocked again for 45 minutes at room temperature. Subsequently the tissue sections were incubated in either Alexafluor 594-conjugated goat-anti-rabbit IgG or goat-anti mouse (1:500, Invitrogen) for 1 hour at 4° C. Rinsed sections were mounted and fluorescence was visualized using a Zeiss LM 780 confocal microscope in the UNC Neuroscience imaging core. GFP co-localization was determined on the Z axis.

Patch Clamp Electrophysiology: Electrophysiological recordings were obtained from GFP fluorescent cells in both current-clamp and voltage-clamp modes using standard electrophysiological techniques (Ming et al., *Alcohol Clin. Exp. Res.* 30:1400 (2006)). Briefly, 300μ coronal vibrotome sections were cut in oxygenated (95% O₂/5% CO₂) ice cold, bicarbonate-buffered artificial CSF. After a 1 h incubation in that ACSF at room temperature (22° C.), samples were transferred to a flow chamber containing room temperature ACSF. Whole-cell patch recordings were obtained from fluorescent cells using a high Cl⁻ internal-solution as previously described (Ming et al., *Alcohol Clin. Exp. Res.* 30:1400 (2006)). Neurons were clamped to −60 mV for voltage-clamp recording and either, maintained at their normal resting potential or forced to −60 mV by current injection for current-clamp recording. Brief (300 ms) current injections were administered during voltage clamp for some cells to elicit an action potential.

Example 2

Transdifferentiation of Oligodendrocytes

The approach taken to in vivo transdifferentiation of oligodendrocytes into neurons relied upon two recent observations. Xue et al. (Cell 152:82 (2013)) reported that suppression of polypyrimidine-tract-binding (PTB) protein expression in cultured fibroblasts caused a portion of the fibroblasts to differentiate into functional neurons. Thus, manipulation of a single factor could induce neuronal reprogramming. Secondly, a novel AAV vector was recently developed where the chimeric capsid confers a dominant oligodendrocyte tropism in the rat striatum. Based upon these two findings, 2 siRNAs were identified that significantly inhibited PTBP1 expression in HeLa cells (FIG. 1A) and then these siRNA sequences were converted into miRNAs using the BLOCK-iT™ Pol II miRNAi expression vector kit. Next the miRNA-GFP construct was subcloned into an AAV plasmid where the gene expression is driven by a hybrid chicken-beta actin promoter. Recombinant AAV serotype 2 virus was produced with this construct and the Olig001 AAV vector (described in WO 2016/081811, incorporated herein by reference in its entirety) and this virus was used to transduce HEK293 cells in vitro. Subsequent western blots established that the virus derived miRNA gene expression substantially reduced the expression of PTBP1 (FIG. 1A).

Figure 1B:
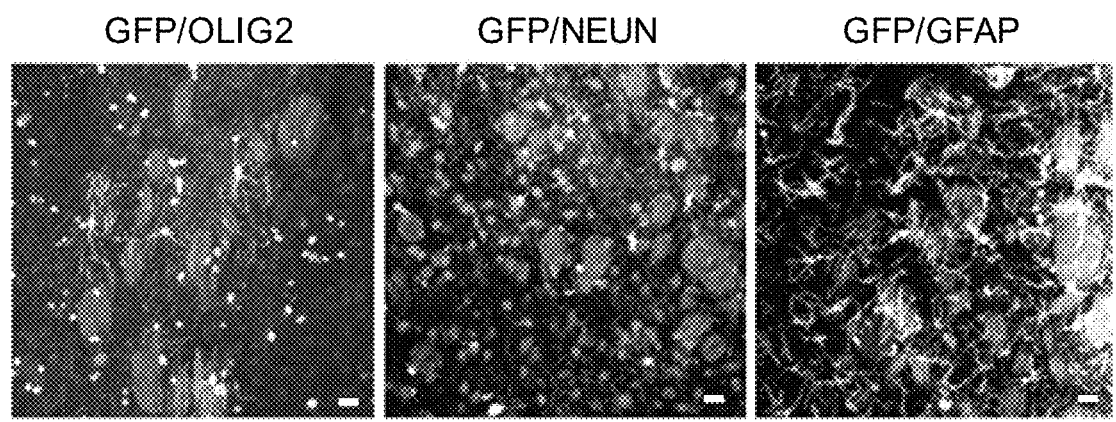
Figure 1C:
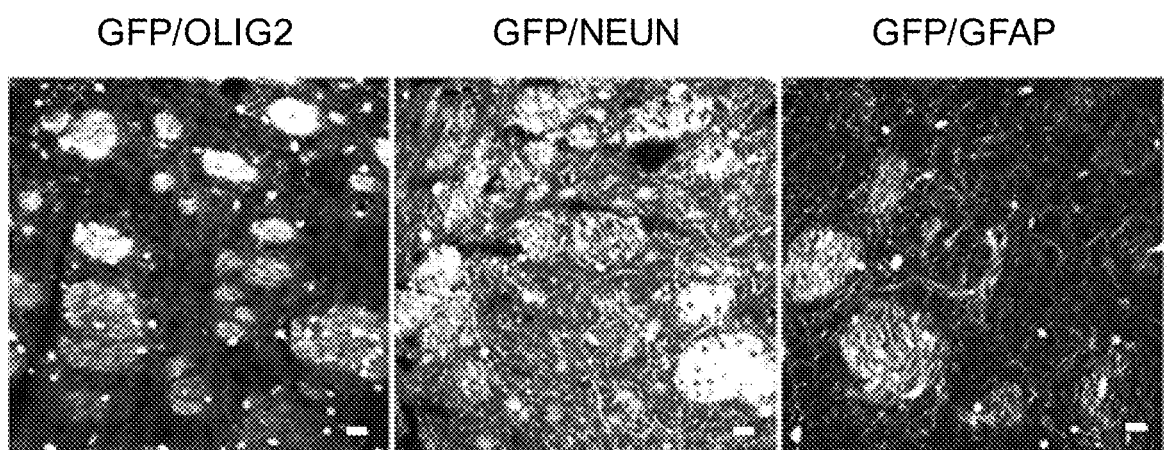
Figure 2:
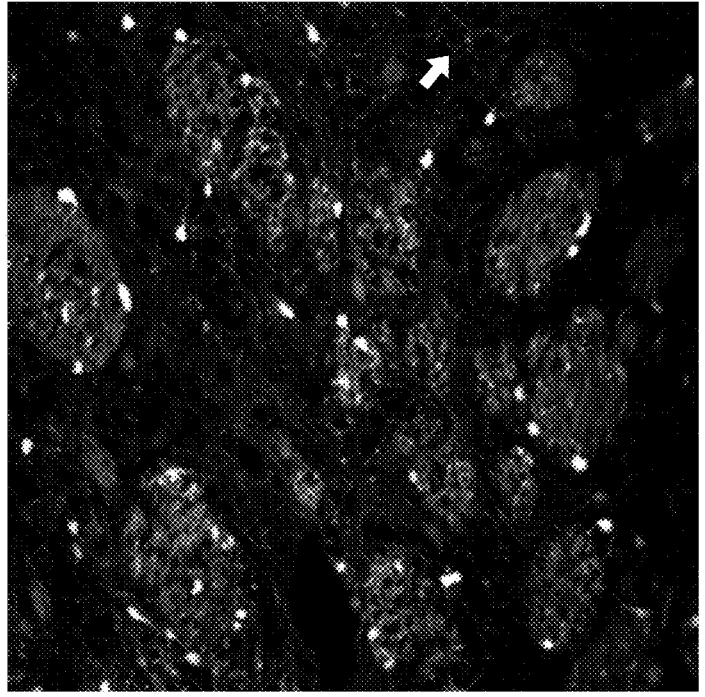
FIG. 2 shows Olig001 AAV-GFP vectors do not transduce dividing cells in the rat striatum. Rats received a 100 mg/kg i.p. dose of BrdU 30 minutes prior to Olig001-AAV-GFP infusion into the striatum and a second 100 mg/kg i.p. dose of BrdU 30 minutes post-vector infusion. Two weeks later, as expected very few dividing cells were found in the striatum, although this labeling protocol resulted in many BrdU positive cells in the sub-granular zone of the dentate gyrus. As seen in the confocal image the dividing cell (white arrow) did not co-localize with the GFP positive cells. No instances of GFP/BrdU co-localization were found throughout the areas of transduction for 2 rats. (horizontal bars=20 microns).

As noted above, an advantageous component to this reprogramming approach involved the ability to target preferentially oligodendrocytes in vivo where gene expression was driven by a promoter active in both oligodendrocytes and neurons. As seen in FIG. 1B, after direct striatal injection recombinant AAV-GFP vectors containing the oligotropic capsid almost exclusively transduced oligodendrocytes in the rat striatum. Ten days post-infusion, the GFP positive cells exhibit the classic morphology of striatal oligodendrocytes including the dramatic presence of GFP in striatal patches that were composed primarily of myelinated projection axons. Moreover, the GFP positive cells did not co-localize with NeuN, a marker of neurons, or GFAP, a marker of astrocytes, but did co-localize with Olig2, a marker of oligodendrocytes (FIG. 1B). Also, this vector did not transduce dividing cells in the striatum, because 5-bromo-2-deoxyuridine (BrdU) administration during the initial period of AAV GFP transduction resulted in a total absence of GFP co-localization with BrdU-labeled striatal cells 2 weeks later (FIG. 2). Most importantly, this dominant oligodendrocyte transduction pattern remained stable over time, given that the same oligodendrocyte transduction pattern was observed 6 months post-transduction (FIG. 1C). Thus, this AAV vector provided the ability to use a constitutive promoter to express the PTBP1 miRNA predominantly in striatal oligodendrocytes, but also subsequently in transdifferentiated cells.

Figures 3A, 3B:
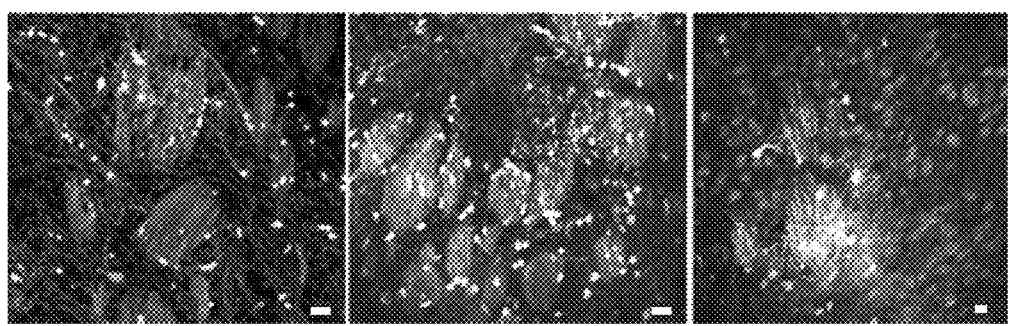

The miRNA-GFP construct was packaged into recombinant AAV vectors using the oligodendrocyte preferring capsid plasmid and directly injected into the rat striatum. Ten days later the majority of GFP positive cells exhibited oligodendrocyte morphology including a substantial GFP presence in the striatal patch, co-localized with the oligodendrocyte marker, Olig2, but did not co-localize with NeuN (FIG. 3A). However, over time these transduced oligodendrocytes transdifferentiated into functional striatal neurons. As seen in FIG. 3B, by 6 weeks post-transduction, the majority of the GFP positive cells exhibited the typical morphology of striatal neurons where the GFP co-localized with NeuN. Also, there was a marked absence of GFP in the striatal patches, and some of the GFP positive cells co-localized with DARRP32, or parvalbumin, both markers for subclasses of GABAergic striatal neurons (FIG. 3B). As importantly, these transdifferentiated neurons remained present at 3 and 6 months post-striatal transduction, with little evidence of GFP positive oligodendrocytes (FIG. 3C).

Although the transdifferentiated cells exhibited many morphological and immunohistochemical properties indicative of striatal neurons, the question remained whether these cells were functional neurons. To address this question, patch-clamp recordings were obtained from striatal slices either 6 weeks (3 cells) or 3 months (3 cells) post-AAV miRNA-GFP transduction. Action potentials were recorded from 6 of 6 fluorescent cells where these action potentials occurred spontaneously in 4 of 6 cells during voltage clamp at −60 mV and in 4 of 5 during current clamp (FIG. 4A). In the 2 cells that did not exhibit spontaneous action potentials, action-potentials were elicited by a 300 ms current injection. Spontaneous post-synaptic currents were observed in 5 of 6 cells examined (FIG. 4B). These spontaneous post-synaptic currents indicate that the recorded neurons were responding to neuronal inputs. Resting-potential values were determined in 5 of the 6 neurons and ranged from a low of −26 mV to a high of −71 mV, with a mean of −47.6 mV.

Further functional validation was obtained by the presence and function of GFP positive terminals in two areas of striatal projection, the globus pallidus and the substantia nigra. Normally, striatal transduction with theOlig001 AAV GFP vector does not result in GFP positive terminals in the globus pallidus or substantia nigra. However, GFP positive axon terminals were present in the globus pallidus and the substantia nigra 3 months after striatal transduction by the AAV4 miRNA GFP vectors (FIG. 4C). In order to test the functional nature of these terminals, 0.04 micron fluorescent beads were infused into either the globus pallidus or the substantia nigra, 3 months after striatal AAV-miRNA-GFP vector administration. Two weeks later the rats were sacrificed and GFP-fluorescent bead co-localization was determined. Confocal microscopy identified a number of GFP positive striatal cells that contained the fluorescent beads from either the globus pallidus or the substantia nigra (FIG. 4C). Thus, the GFP positive presynaptic terminals proved capable of internalizing the fluorescent beads and retrogradely transporting the beads back to the striatal cell body. The presence of this retrograde axonal transport indicates functional presynaptic terminals.

The present results demonstrate that a single non-toxic AAV vector can induce the transdifferentiation of resident oligodendrocytes into functional neurons in the rat striatum. This oligodendrocyte reprogramming produces cells that exhibit morphological, immunhistochemical and electro-physiological properties of mature striatal neurons. Olig001 capsid AAV4 miRNA GFP-transduced striatal cells initially exhibited morphological and immunohistochemical properties unique to oligodendrocytes, similar to striatal transduction by control Olig001 capsid AAV GFP vectors. However, in marked contrast to control Olig001 capsid AAV GFP vectors, by 6 weeks prost treatment the transduced cells exhibited morphological, immunohistochemical, and electrophysiological properties unique to mature striatal neurons. Since Olig001 AAV GFP-transduced cells did not co-localize with BrdU-labeled cells, this transition was not due to a differentiation of dividing progenitor cells. Furthermore, many of the transdifferentiated neurons expressed cellular markers indicative of subclasses of striatal neurons, so it is likely that the striatal milieu exerts a significant influence on the fate of transdifferentiated cells. Also, the occurrence of inhibitory postsynaptic currents indicates that these transdifferentiated neurons have integrated into the local circuitry, while the presence of distal axonal projections and functional retrograde transport suggest some level of structure-appropriate, distal integration. These measures strongly support the presence of functional transdifferentiated neurons.

An advantageous element to this neuronal replacement strategy involved the ability to express the gene product over the course of the initial transduction, as well as in the subsequent transdifferentiated cell. The vast majority of AAV serotypes exhibit a predominant neuronal tropism, when gene expression is driven by a constitutive promoter. However, previous studies have shown that AAV8 or AAV1/2 scrotypes can selectively support in vivo oligodendrocyte gene expression, but this oligodendrocyte tropism requires the use of oligodendrocyte-specific promoters, such as myelin basic protein. Because the oligodendrocyte-specific promoter is not active in a neuron, as the oligodendrocyte transdifferentiates into a mature neuron, the resumption of PTB protein expression likely would reprogram the transdifferentiated neuron back to an oligodendrocyte or a cellular intermediate. By employing the Olig001 capsid AAV vector and a constitutive promoter, striatal gene expression was driven both in the initial transduced oligodendrocytes and in the subsequent transdifferentiated neurons. Certainly, the long-term PTB protein repression proved effective, as evidenced by the presence of transdifferentiated neurons 6 months post-transduction.

Another property of this vector-derived in vivo transdifferentiation involved the overall relative efficacy. By 6 weeks post-transduction, substantial numbers of the GFP-positive cells in the striatum exhibited neuronal properties with very few remaining GFP-positive oligodendrocytes or GFP-labeled striatal patches. In comparison, lentiviral-mediated suppression of PTB protein expression achieved an 8%-15% efficacy for in vitro embryonic fibroblast re-programming, while retroviral expression of ND4 and Insm1 induced 40% of cultured astrocytes to differentiate into neuronal-like cells. One possible explantation for these differences could be the fact that our viral vector approach selectively targets endogenous cells within the CNS.

The foregoing is illustrative of the present invention, and is not to be construed as limiting thereof. The invention is defined by the following claims, with equivalents of the claims to be included therein.

---

We claim:

1. A vector comprising a polynucleotide encoding an antisense RNA or an interfering RNA that hybridizes to a polynucleotide encoding a human polypyrimidine tract binding protein 1 (PTBP1), wherein the antisense RNA or interfering RNA is a siRNA, shRNA, and/or miRNA, wherein the polynucleotide encoding the antisense or interfering RNA encodes for a siRNA, shRNA, and/or miRNA comprising a single polynucleotide strand, the single polynucleotide strand comprising a nucleotide sequence with at least 85% sequence identity to SEQ ID NO: 4 and a nucleotide sequence with at least 85% sequence identity to the complement of SEQ ID NO: 4, and wherein the vector is a delivery vector.

2. The vector of claim 1, wherein the vector is in a viral vector.

3. The vector of claim 2, wherein the viral vector is an adeno-associated virus (AAV) vector.

4. The vector of claim 3, wherein the AAV vector has a tropism for oligodendrocytes and/or oligodendrocyte precursor cells, and wherein the vector is an Olig001 vector.

5. The vector of claim 1, wherein the vector is a lipid vector, poly-lysine vector, or synthetic polyamino polymer vector.

6. The vector of claim 1, wherein the interfering RNA is a siRNA.

7. The vector of claim 1, wherein the polynucleotide encoding the antisense or interfering RNA encodes for a siRNA, shRNA, and/or miRNA comprising a single polynucleotide strand, the single polynucleotide strand comprising a nucleotide sequence with at least 90% sequence identity to SEQ ID NO: 4 and a nucleotide sequence with at least 90% sequence identity to the complement of SEQ ID NO: 4.

8. The vector of claim 1, wherein the polynucleotide is operably linked to a promoter.

9. The vector of claim 8, wherein the promoter is a constitutive promoter.

10. The vector of claim 8, wherein the promoter is a tissue-specific promoter.

11. A pharmaceutical composition comprising the vector of claim 1 and a pharmaceutically acceptable carrier.

\* \* \* \* \*

SEQUENCE LISTING

```
Sequence total quantity: 12
SEQ ID NO: 1           moltype = RNA  length = 19
FEATURE                Location/Qualifiers
source                 1..19
                       mol_type = other RNA
                       organism = synthetic construct
SEQUENCE: 1
```

-continued

```
cggcatcgtc ccagacata                                                 19

SEQ ID NO: 2            moltype = RNA   length = 19
FEATURE                 Location/Qualifiers
source                  1..19
                        mol_type = other RNA
                        organism = synthetic construct
SEQUENCE: 2
caatggcggt gtggtcaaa                                                 19

SEQ ID NO: 3            moltype = RNA   length = 19
FEATURE                 Location/Qualifiers
source                  1..19
                        mol_type = other RNA
                        organism = synthetic construct
SEQUENCE: 3
caacttgaac cctgagaga                                                 19

SEQ ID NO: 4            moltype = RNA   length = 19
FEATURE                 Location/Qualifiers
source                  1..19
                        mol_type = other RNA
                        organism = synthetic construct
SEQUENCE: 4
ccaacactat ggttaacta                                                 19

SEQ ID NO: 5            moltype = DNA   length = 64
FEATURE                 Location/Qualifiers
source                  1..64
                        mol_type = other DNA
                        organism = synthetic construct
SEQUENCE: 5
tgctgtctct cagggttcaa gttgctgttt tggccactga ctgacagcaa cttaccctga   60
gaga                                                                 64

SEQ ID NO: 6            moltype = DNA   length = 64
FEATURE                 Location/Qualifiers
source                  1..64
                        mol_type = other DNA
                        organism = synthetic construct
SEQUENCE: 6
cctgtctctc agggtaagtt gctgtcagtc agtggccaaa acagcaactt gaaccctgag   60
agac                                                                 64

SEQ ID NO: 7            moltype = DNA   length = 64
FEATURE                 Location/Qualifiers
source                  1..64
                        mol_type = other DNA
                        organism = synthetic construct
SEQUENCE: 7
tgctgtagtt aaccatagtg ttggcagttt tggccactga ctgactgcca acaatggtta   60
acta                                                                 64

SEQ ID NO: 8            moltype = DNA   length = 64
FEATURE                 Location/Qualifiers
source                  1..64
                        mol_type = other DNA
                        organism = synthetic construct
SEQUENCE: 8
cctgtagtta accattgttg gcagtcagtc agtggccaaa actgccaaca ctatggttaa   60
ctac                                                                 64

SEQ ID NO: 9            moltype = DNA   length = 31
FEATURE                 Location/Qualifiers
source                  1..31
                        mol_type = other DNA
                        organism = synthetic construct
SEQUENCE: 9
agctgcggcc gcagggaggt agtgagtcga c                                   31

SEQ ID NO: 10           moltype = DNA   length = 32
FEATURE                 Location/Qualifiers
source                  1..32
                        mol_type = other DNA
                        organism = synthetic construct
SEQUENCE: 10
tcatgcggcc gcgaaagctg ggtctagata tc                                  32

SEQ ID NO: 11           moltype = DNA   length = 19
```

-continued

```
FEATURE              Location/Qualifiers
source               1..19
                     mol_type = other DNA
                     organism = synthetic construct
SEQUENCE: 11
cgacaaccac tacctgagc                                          19

SEQ ID NO: 12        moltype = DNA  length = 3281
FEATURE              Location/Qualifiers
source               1..3281
                     mol_type = genomic DNA
                     organism = Homo sapiens
SEQUENCE: 12
ctcggagccg ttgggtcggt tcctgctatt ccggcgcctc cactccgtcc cccgcgggtc   60
tgctctgtgt gccatggacg gcattgtccc agatatagcc gttggtacaa agcggggatc  120
tgacgagctt ttctctactt gtgtcactaa cggaccgttt atcatgagca gcaactcggc  180
ttctgcagca aacggaaatg acagcaagaa gttcaaaggt gacagccgaa gtgcaggcgt  240
cccctctaga gtgatccaca tccggaagct ccccatcgac gtcacggagg gggaagtcat  300
ctccctgggg ctgccctttg ggaaggtcac caacctcctg atgctgaagg ggaaaaacca  360
ggccttcatc gagatgaaca cggaggaggc tgccaacacc atggtgaact actcacacct  420
ggtgacccct gtgctgcgcg gccagcccat ctacatccag ttctccaacc acaaggagct  480
gaagaccgac agctctccca accaggcgcg ggcccaggcg gccctgccag cggtgaactc  540
ggtccagtcg gggaacctgg ccttggctgc ctcggcggcg gccgtggacg cagggatggc  600
gatggccggg cagagccccg tgctcaggat catcgtggag aacctcttct accctgtgac  660
cctggatgtg ctgcaccaga ttttctccaa gttcggcaca gtgttgaaga tcatcacctt  720
caccaagaac aaccagttcc aggccctgct gcagtatgcg gacccgtga gcgcccagca  780
cgccaagctg tcgctggacg ggcagaacat ctacaacgcc tgctgcacgc tgcgcatcga  840
cttttccaag ctcaccagcc tcaacgtcaa gtacaacaat gacaagagcc gtgactacac  900
acgcccagac ctgccttccg gggacagcca gccctcgctg gaccagacca tggccgcggc  960
cttcggtgca cctggtataa tctcagcctc tccgtatgca ggagctggtt tccctcccac 1020
ctttgccatt cctcaagctg caggcctttc cgttccgaac gtccacggcg ccctggcccc 1080
cctggccatc ccctcggcgg cggcggcagc tgcggcggca ggtcggatcg ccatcccggg 1140
cctggcgggg gcaggaaatt ctgtattgct ggtcagcaac ctcaacccag agagagtcac 1200
accccaaagc ctctttattc ttttcggcgt ctacggtgac gtgcagcgcg tgaagatcct 1260
gttcaataag aaggagaacg ccctagtgca gatggcggac ggcaaccagg cccagctggc 1320
catgagccac ctgaacgggc acaagctgca cgggaagccc atccgcatca cgctctcgaa 1380
gcaccagaac gtgcagctgc cccgcgaggg ccaggaggac cagggcctga ccaaggacta 1440
cggcaactca cccctgcacc gcttcaagaa gccgggctcc aagaacttcc agaacatatt 1500
cccgccctcg gccacgctgc acctctccaa catcccgcc tcagtctccg aggaggatct 1560
caaggtcctg ttttccagca atgggggcgt cgtcaaagga ttcaagttct tccagaagga 1620
ccgcaagatg gcactgatcc agatgggctc cgtggaggag gcggtccagg ccctcattga 1680
cctgcacaac cacgacctcg gggagaacca ccacctgcgg gtctccttct ccaagtccac 1740
catctagggg cacaggcccc cacggccggg cccctggcg acaacttcca tcattccaga 1800
gaaaagccac tttaaaaaca gctgaagtga ccttagcaga ccagagattt tattttttta 1860
aagagaaatc agtttacctg ttttttaaaaa aattaaatct agttcacctt gctcaccctg 1920
cggtgacagg gacagctcag gctcttggtg actgttgcag cgggagttcc cggccctcca 1980
caccggggc cagaccctcg gggccatgcc ttggtggggc ctgtgtcggg cgtggggcct 2040
gcaggtgggc gccccgacca cgacttggct tccttgtgcc ttaaaaaacc tgccttcctg 2100
cagccacaca cccacccggg gtgtcctggg gacccaaggg gtggggggt cacaccagag 2160
agaggcaggg ggcctggccg gctcctgcag gatcatgcag ctggggcgcg gcggccgcgg 2220
ctgcgacacc ccaaccccag ccctctaatc aagtcacgtg attctccctt cacccgccc 2280
ccagggcctt cccttctgcc cccaggcggg ctccccgctg ctccagctgc ggagctggtc 2340
gacataatct ctgtattata tactttgcag ttgcagacgt ctgtgcctag caatatttcc 2400
agttgaccaa atattctaat cttttttcat ttatatgcaa aagaaatagt tttaagtaac 2460
tttttatagc aagatgatac aatggtatga gtgtaatcta aacttccttg tggtattacc 2520
ttgtatgctg ttacttttat tttattcctt gtaattaagt cacaggcagg acccagtttc 2580
cagagagcag gcggggccgc ccagtgggtc aggcacaggg agccccggtc ctatcttaga 2640
gccctgagc ttcagggaag gggcgggcgt gtcgccgcct ctggcatcgc ctccggttgc 2700
cttacaccac gccttcacct gcagtcgcct agaaaacttg ctctcaaact tcagggtttt 2760
ttcttccttc aaattttgga ccaaagtctc atttctgtgt tttgcctgcc tctgatgctg 2820
ggacccggaa ggcgggcgct cctcctgtct ttgtgctctt tctaccgccc ccgcgtcctg 2880
tcccgggggc tctcctagga tccccttcc gtaaagcgt gtaacaaggg tgtaaatatt 2940
tataatttt tatacctgtt gtgagacccg aggggcggcg gcgcggtttt ttatggtgac 3000
acaaatgtat attttgctaa cagcaattcc aggctcagta ttgtgaccgc ggagccacag 3060
gggacccac gcacattccg ttgccttacc cgatggcttg tgacgcggag agaaccgatt 3120
aaaaccgttt gagaaactcc tcccttgtct agccctgtgt tcgctgtgga cgctgtagag 3180
gcaggttggc cagtctgtac ctggacttcg aataaatctt ctgtatcctc aaaaaaaaaa 3240
aaaaaaaaa aaaaaaaaa aaaaaaaaa aaaaaaaaa a                    3281
```